(12) United States Patent
Gargallo Viola et al.

(10) Patent No.: US 9,840,467 B2
(45) Date of Patent: Dec. 12, 2017

(54) ARYLHYDRAZIDES CONTAINING A 2-PYRIDONE MOIETY AS SELECTIVE ANTIBACTERIAL AGENTS

(71) Applicant: ABAC THERAPEUTICS, S.L., Barcelona (ES)

(72) Inventors: Domingo Gargallo Viola, Barcelona (ES); Albert Palomer Benet, Barcelona (ES)

(73) Assignee: ABAC THERAPEUTICS, S.L., Barcelona (ES)

(*) Notice: Subject to any disclaimer, the term of this patent is extended or adjusted under 35 U.S.C. 154(b) by 0 days.

(21) Appl. No.: 15/500,333

(22) PCT Filed: Jul. 29, 2015

(86) PCT No.: PCT/EP2015/067345
§ 371 (c)(1),
(2) Date: Jan. 30, 2017

(87) PCT Pub. No.: WO2016/016291
PCT Pub. Date: Feb. 4, 2016

(65) Prior Publication Data
US 2017/0217887 A1    Aug. 3, 2017

(30) Foreign Application Priority Data
Jul. 30, 2014  (EP) .................................. 14179089

(51) Int. Cl.
*C07D 211/90* (2006.01)
*A61K 31/4412* (2006.01)

(52) U.S. Cl.
CPC ................................. *C07D 211/90* (2013.01)

(58) Field of Classification Search
None
See application file for complete search history.

(56) References Cited

FOREIGN PATENT DOCUMENTS

| WO | WO 2004/043924 A1 * | 5/2004 |
| WO | WO 2004/043924 A1 | 5/2004 |
| WO | WO 2012/051708 A1 | 4/2012 |

OTHER PUBLICATIONS

Written Opinion of the International Search Authority for PCT/EP2015/067345, dated Oct. 22, 2015.*
Database Registry, "Registry No. 1061187-80-1," Oct. 14, 2008, 1 page, XP-002733431.
Database Registry, "Registry No. 1298649-45-2," May 22, 2011, 1 page, XP-002733427.
Database Registry, "Registry No. 1317306-41-4," Aug. 14, 2011, 1 page, XP-002733430.
Database Registry, "Registry No. 1424347-10-3," Mar. 15, 2013, 1 page, XP-002733429.
Database Registry, "Registry No. 356583-19-2," Sep. 13, 2001, 1 page, XP-002733428.
Giamarellou et al., "Acinetobacter baumannii: A Universal Threat to Public Health?" International Journal of Antimicrobial Agents, vol. 32, 2008, pp. 106-119.
Howard et al., "Acinetobacter baumannii, An Emerging Opportunistic Pathogen," Virulence, vol. 3, Issue 3, May/Jun. 2012, pp. 243-250.
Jernberg et al., "Long-term Impacts of Antibiotic Exposure on the Human Intestinal Microbiota," Microbiology, vol. 156, 2010, pp. 3216-3223.
Villarreal et al., "Use of Broad-Spectrum Antibiotics and the Development of Irritable Bowel Syndrome," WMJ, vol. 111, No. 1, Feb. 2012, pp. 17-20 (Total 5 pages).
Weber, "Decker Oxidation of 2-substituted N-alkylpyridinium Compounds, Part 5, The Decker Oxidation of Homarine," Arch. Pharm, vol. 309, 1976, pp. 664-669 (Total 12 pages), with an English translation.

* cited by examiner

*Primary Examiner* — Zinna Northington-Davis
(74) *Attorney, Agent, or Firm* — Birch, Stewart, Kolasch & Birch, LLP

(57) ABSTRACT

The present invention belongs to the field of antibacterial agents, more specifically to antibacterials for treating *Acinetobacter baumannii* infections. The invention provides arylhydrazides containing a 2-pyridone moiety, according to formula (I), which show selective antibacterial activity against *A. baumannii*. The invention also relates to their use as medicaments and specifically as antibacterials for the treatment of *A. baumannii* infections, as well as to a process for their preparation and to pharmaceutical compositions containing them.

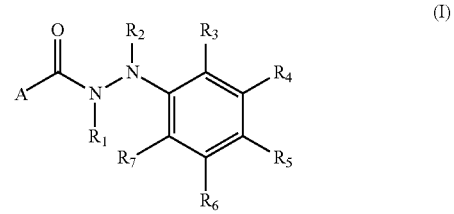

27 Claims, No Drawings

ARYLHYDRAZIDES CONTAINING A 2-PYRIDONE MOIETY AS SELECTIVE ANTIBACTERIAL AGENTS

TECHNICAL FIELD

The present invention relates to new antibacterial agents, particularly to arylhydrazide compounds containing a 2-pyridone moiety that show selective antibacterial activity against the Gram-negative bacteria *Acinetobacter baumannii*.

BACKGROUND ART

Infections caused by *Acinetobacter baumannii* (*A. baumannii*) bacteria are increasingly recognized as a serious health threat, especially in healthcare facilities, and are associated with increased morbidity, mortality and duration of hospital stay, as well as with high healthcare costs (Giamarellou et al. *Acinetobacter baumannii*: a universal threat to public health? Int. J. Antimicrob. Agents, 2008, 32(2), 106-9; Howard et al. *Acinetobacter baumannii*. An emerging opportunistic pathogen. Virulence 2012, 3(3), 243-250).

*A. baumannii* is a rod-shaped Gram-negative *bacillus* that is aerobic, and non-motile. It behaves as an opportunistic pathogen mainly affecting immunocompromised subjects, for example those having an underlying disease, such as chronic lung disease or diabetes, and those hospitalized for long periods and subjected to multiple invasive procedures.

*A. baumannii* is often implicated in nosocomial infections, so it has a high incidence among patients experiencing prolonged hospital stay, and is a particularly relevant source of infections in hospital intensive care units (ICUs). Among the main risk factors for acquiring *A. baumannii* is the use of artificial devices commonly employed in hospital settings, such as dialysis, mechanical ventilation, sutures or catheters, due to the notorious ability of *A. baumannii* to survive for extended periods on environmental surfaces.

*A. baumannii* can cause infections in virtually every organ system of the human body, including pneumonia, surgical site infections, skin and soft tissue infections, urinary tract infections, post-operative meningitis and catheter-related infections.

Hospital-acquired pneumonia is the most common life-threatening hospital-acquired infection, and is mainly associated with the use of mechanical ventilation, known as ventilator associated pneumonia (VAP). VAP infections caused by *Acinetobacter* are between 8% and 35% of total VAP cases.

Bloodstream infections (BSI) are also common nosocomial infections, which are also associated with increased morbidity, mortality and duration of hospital stay. Infections caused by *Acinetobacter* correspond to 2% of the total BSI cases, with a particular high incidence in ICU-acquired BSI.

Other reported hospital-acquired infections associated with *A. baumannii* are, for example, surgical site infections (SSI) and urinary tract infections, such as catheter-associated urinary tract infections (CAUTI) or hospitalized community-acquired urinary tract infections.

*A. baumannii* infections are currently treated with different broad- or semi-broad spectrum antibiotics or combinations, including, for example, the carbapenems imipenem, meropenem and doripenem, which are first choice drugs. However, treatment of *A. baumannii* infections is challenging since it has emerged as a highly drug-resistant pathogen, especially carbapenem-resistant, and therefore other alternative broad-spectrum antibacterials are also used in therapy, such as polymyxins (colistin, polymyxin E and polymyxin B), tigecycline, tetracyclines (minocycline and doxycycline) or aminoglycosides (amikacin and tobramycin). None of the currently used treatments are specific for *A. baumannii*.

The use of such broad-spectrum antibacterials entails important drawbacks, since they have a substantial impact on the normal flora, potentially diminishing the immunologic function of microbiota and potentially generating treatment-induced co-infections caused by resistant strains, as disclosed for example in Jernberg et al. *Long-term impacts of antibiotic exposure on the human intestinal microbiota*, Microbiology, 2010, 156(Pt 11), 3216-3223.

Moreover, in a retrospective study performed with 26,107 patients, it was concluded that the use of broad-spectrum antibiotics may have a relationship with the development of irritable bowel syndrome (IBS), as disclosed in Villarreal et al. *Use of broad-spectrum antibiotics and the development of irritable bowel syndrome*, WMJ, 2012, 111(1), 17-20.

In contrast, treatments using pathogen-specific antibacterials that kill exclusively the infecting bacteria would minimize the impact on normal flora and would avoid the selection of resistant strains of non-infecting bacteria of microbiota, thus minimizing any treatment-induced co-morbidities.

To date, the only pathogen-specific compound that has been described in prior art is a synthetic cyclo-peptide known by the laboratory code POL7080, that is currently under clinical development. It has been reported that POL7080 has antimicrobial activity exclusively against *Pseudomonas* bacteria but, conversely, shows no activity against *Acinetobacter* bacteria.

Therefore, there is still a need to develop new antibacterial agents that are effective for treating the life-threatening infections caused by *Acinetobacter* bacteria and that also show a selective antimicrobial pattern to avoid the disadvantages associated to the non-selective broad-spectrum antibiotics currently used in therapy.

OBJECT OF THE INVENTION

The object of the present invention is a compound of formula (I) as defined below.

A second aspect of the present invention relates to the compound of formula (I) for use as a medicament.

A third aspect of the present invention relates to a compound of formula (I) for use as antibacterial agent, particularly for treating or preventing *A. baumannii* infections.

A further aspect of the present invention relates to the use of a compound of formula (I) for the manufacture of a medicament.

A further aspect of the present invention relates to the use of a compound of formula (I) for the manufacture of an antibacterial agent, preferably for treating or preventing *A. baumannii* infections.

A further aspect of the present invention relates to a method for the treatment or prevention of bacterial infections in a subject in need thereof, comprising administering an effective amount of a compound of formula (I), preferably for treating of preventing *A. baumannii* infections.

A further aspect of the present invention relates to a pharmaceutical composition comprising a compound of formula (I) and at least one pharmaceutically acceptable excipient and/or carrier.

A further aspect of the present invention relates to a process for preparing compounds of formula (I).

DETAILED DESCRIPTION OF THE INVENTION

In a first aspect, the present invention relates to a compound of formula (I):

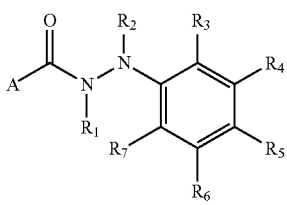

or a pharmaceutically acceptable salt or solvate thereof, wherein
A is a radical selected from $A_1$, $A_2$, $A_3$ and $A_4$;
$A_1$ is

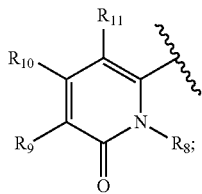

$A_2$ is

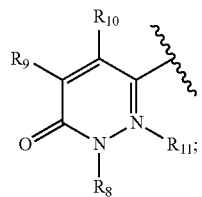

$A_3$ is

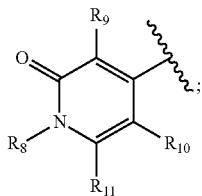

$A_4$ is

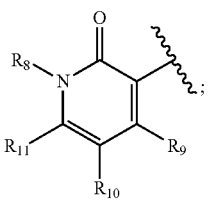

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$;

$R_8$ is selected from $C_{1-6}$alkyl, $C_{2-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl, Ph$C_{1-4}$alkyl and —$C_{1-4}$alkyl-$CONR_{12}R_{13}$;

$R_9$, $R_{10}$ and $R_{11}$ are independently selected from hydrogen, $C_{1-6}$alkyl, $C_{3-6}$cycloalkyl$C_{1-4}$alkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$; and each $R_{12}$ and $R_{13}$ are independently selected from hydrogen and $C_{1-4}$alkyl;

with the proviso that the following products are excluded:
1-methyl-6-oxo-1,6-dihydro-pyridine-2-carboxylic acid N'-phenylhydrazide,
1-benzyl-2-oxo-1,2-dihydro-pyridine-3-carboxylic acid N'-(2-(trifluoromethyl)phenyl)-hydrazide,
1-benzyl-4,6-dimethyl-2-oxo-1,2-dihydro-pyridine-3-carboxylic acid N'-phenyl-hydrazide,
1-methyl-2-oxo-1,2-dihydro-pyridine-4-carboxylic acid N'-(2,4,6-trichlorophenyl)-hydrazide,
1-((3-methylphenyl)methyl)-2-oxo-1,2-dihydro-pyridine-3-carboxylic acid N'-(3-(trifluoromethyl)phenyl)-hydrazide and
1-((2-chlorophenyl)methyl)-6-oxo-1,6-dihydro-pyridine-3-carboxylic acid N'-phenyl-N'-methyl-hydrazide.

The authors of the present invention have developed a group of arylhydrazides containing a 2-pyridone moiety as depicted in formula (I) that, surprisingly, show selective antibacterial activity against the Gram-negative bacteria *A. baumannii*, providing therefore a new therapeutic tool for treating the infections caused by this bacteria in a safer way, while avoiding the damage to the intestinal flora and multiple resistances involved with the treatment with the current broad-spectrum antibacterials.

There is no disclosure in the prior art of 2-pyridone substituted arylhydrazides showing antibacterial activity. Moreover, there is no previous disclosure of antibacterial agents showing selectivity against *A. baumannii* bacteria.

In the article Weber H., Decker-oxidation 2-substituierter N-Alkylpyridiniumverbindungen, 5 Mitt. Die Decker-Oxidation von Homarin. Archiv. Pharm. 1976, 309 (8), 664-9, in the context of the use of the Decker oxidation for the oxidation of homarine, the preparation of the product 1-methyl-6-oxo-1,6-dihydro-pyridine-2-carboxylic acid N'-phenylhydrazide is disclosed, which falls within the general scope of formula (I). However, there is no disclosure or suggestion about any therapeutic activity of this compound. The product 1-methyl-6-oxo-1,6-dihydro-pyridine-2-carboxylic acid N'-phenylhydrazide is therefore excluded from the first aspect of the invention related to the compounds of formula (I) and it is also specifically excluded from all the more specific embodiments of this first aspect where it is encompassed.

Moreover, the following compounds from chemical libraries fall within the general scope of formula (I): 1-benzyl-2-oxo-1,2-dihydro-pyridine-3-carboxylic acid N'-(2-(trifluoromethyl)phenyl)-hydrazide (CAS 1298649-45-2), 1-benzyl-4,6-dimethyl-2-oxo-1,2-dihydro-pyridine-3-carboxylic acid N'-phenyl-hydrazide (CAS 356583-19-2), 1-methyl-2-oxo-1,2-dihydro-pyridine-4-carboxylic acid N'-(2,4,6-trichlorophenyl)-hydrazide (CAS 1424347-10-3), 1-((3-methylphenyl)methyl)-2-oxo-1,2-dihydro-pyridine-3-carboxylic acid N'-(3-(trifluoromethyl)phenyl)-hydrazide (CAS 1317306-41-4) and 1-((2-chlorophenyl)methyl)-6-oxo-1,6-dihydro-pyridine-3-carboxylic acid N'-phenyl-N'-methyl-hydrazide (CAS 1061187-80-1). However, these products are merely listed in the chemical libraries, without any further information being provided, particularly about their preparation. Furthermore, no disclosure or suggestion about any therapeutic activity of these compounds is reported.

Therefore, in the first aspect of the invention, the following products are excluded:

1-benzyl-2-oxo-1,2-dihydro-pyridine-3-carboxylic acid N'-(2-(trifluoromethyl)phenyl)-hydrazide, 1-benzyl-4,6-dimethyl-2-oxo-1,2-dihydro-pyridine-3-carboxylic acid N'-phenyl-hydrazide, 1-methyl-2-oxo-1,2-dihydro-pyridine-4-carboxylic acid N'-(2,4,6-trichlorophenyl)-hydrazide, 1-((3-methylphenyl)methyl)-2-oxo-1,2-dihydro-pyridine-3-carboxylic acid N'-(3-(trifluoromethyl)phenyl)-hydrazide, and 1-((2-chlorophenyl)methyl)-6-oxo-1,6-dihydro-pyridine-3-carboxylic acid N'-phenyl-N'-methyl-hydrazide.

It is understood that these compounds are also specifically excluded from all the more specific embodiments herein described of the first aspect of the invention in which they are encompassed.

Definitions

Within the meaning of the present invention, the term $C_{1-6}$alkyl, as a group or part of a group, means a straight or branched alkyl chain which contains from 1 to 6 carbon atoms and includes, among others, the groups methyl, ethyl, n-propyl, isopropyl, n-butyl, isobutyl, sec-butyl, tert-butyl, n-pentyl, isopentyl or n-hexyl. Similarly, the term $C_{1-4}$alkyl, as a group or part of a group, means a straight or branched alkyl chain which contains from 1 to 4 carbon atoms and is a subgroup of $C_{1-6}$alkyl which includes the groups methyl, ethyl, n-propyl, isopropyl, n-butyl, isobutyl, sec-butyl and tert-butyl. The terms $C_{1-6}$alkyl and $C_{1-4}$alkyl can also be linked to other groups, such as any of those listed below, from the replacement of one or more hydrogen atoms from a $C_{1-6}$alkyl and $C_{1-4}$alkyl groups with a different substituent or group, in particular by replacement of one hydrogen atom so that the corresponding straight or branched biradical (i.e. straight or branched alkylenyl) is obtained. In the particular case of a straight biradical, the term $C_{1-4}$alkyl refers to a —$(CH_2)_n$— moiety, wherein n is from 1 to 4, and the term $C_{1-6}$alkyl refers to a —$(CH_2)_n$—, wherein n is from 1 to 6.

A $C_{2-6}$alkynyl group means a linear hydrocarbon group which can be straight or branched, which contains from 2 to 6 carbon atoms and containing at least one carbon-carbon triple bond, and includes, among others, the groups ethynyl, 2-propynyl (or propargyl), 2-butynyl and 3-methyl-2-butynyl. Likewise, a $C_{2-4}$alkynyl group means a linear hydrocarbon group which can be straight or branched, which contains from 2 to 4 carbon atoms and containing at least one carbon-carbon triple bond, and is a subgroup of $C_{2-6}$alkynyl which includes, for example, the groups ethynyl, 2-propynyl (or propargyl), and 2-butynyl.

A $C_{2-6}$alkenyl group means a linear hydrocarbon group which can be straight or branched, which contains from 2 to 6 carbon atoms and containing at least one carbon-carbon double bond, and includes, among others, the groups ethenyl (or vinyl), allyl, 1-propenyl, 3-butenyl or 2-methyl-1-propenyl.

Halogen or its abbreviation halo means fluoro, chloro, bromo or iodo.

A halo$C_{1-6}$alkyl group means a group resulting from the replacement of one or more hydrogen atoms from a $C_{1-6}$alkyl group with one or more halogen atoms (i.e. fluoro, chloro, bromo or iodo), which can be the same or different. Examples include, among others, the groups fluoromethyl, difluoromethyl, trifluoromethyl, chloromethyl, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2,2-trifluoroethyl, 2-fluoropropyl, 3-fluoropropyl, 2,2-difluoropropyl, 2,3-difluoropropyl, 2-chloropropyl, 3-chloropropyl, 2,3-dichloropropyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl. Similarly, the halo$C_{1-4}$alkyl group means a group resulting from the replacement of one or more hydrogen atoms from a $C_{1-4}$alkyl group with one or more halogen atoms (i.e. fluoro, chloro, bromo or iodo), which can be the same or different, and is a subgroup of halo$C_{1-6}$akyl. Examples include, among others, the groups fluoromethyl, difluoromethyl, trifluoromethyl, chloromethyl, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2,2-trifluoroethyl, 2-fluoropropyl, 3-fluoropropyl, 2,2-difluoropropyl, 2,3-difluoropropyl, 2-chloropropyl, 3-chloropropyl, 2,3-dichloropropyl, 4-fluorobutyl, 4-chlorobutyl, 4-bromobutyl and nonafluorobutyl.

A hydroxy$C_{1-6}$alkyl group means a group resulting from the replacement of one or more hydrogen atoms from a $C_{1-6}$alkyl group with one or more hydroxy groups. Examples include, among others, the groups hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl, 1-hydroxybutyl, 5-hydroxypentyl, 4-hydroxypentyl, 3-hydroxypentyl, 2-hydroxypentyl, 1-hydroxypentyl, 6-hydroxyhexyl, 5-hydroxyhexyl, 4-hydroxyhexyl, 3-hydroxyhexyl, 2-hydroxyhexyl, and 1-hydroxyhexyl. Similarly, a hydroxy$C_{1-4}$alkyl group means a group resulting from the replacement of one or more hydrogen atoms from a $C_{1-4}$alkyl group with one or more hydroxy groups, and is a subgroup of the hydroxy$C_{1-6}$alkyl group. Examples of hydroxy$C_{1-4}$alkyl group include, for example, hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl and 1-hydroxybutyl.

A $C_{1-4}$alkoxy group, as a group or part of a group, means a group of formula —O$C_{1-4}$alkyl, wherein the $C_{1-4}$alkyl moiety has the same meaning as described above. Examples include methoxy, ethoxy, propoxy, isopropoxy, n-butoxy, isobutoxy, sec-butoxy and tert-butoxy.

A $C_{1-4}$alkoxy$C_{1-6}$alkyl group means a group resulting from the replacement of one or more hydrogen atoms from a $C_{1-6}$alkyl group with one or more $C_{1-4}$alkoxy groups as defined above, which can be the same or different. Examples include, among others, the groups methoxymethyl, ethoxymethyl, propoxymethyl, isopropoxymethyl, butoxymethyl, isobutoxymethyl, sec-butoxymethyl, tert-butoxymethyl, dimethoxymethyl, 1-methoxyethyl, 2-methoxyethyl, 2-ethoxyethyl, 1,2-diethoxyethyl, 1-butoxyethyl, 2-sec-butoxyethyl, 3-methoxypropyl, 2-butoxypropyl, 1-methoxy-2-ethoxypropyl, 3-tert-butoxypropyl, 4-methoxybutyl, 5-methoxypentyl, 4-ethoxypentyl and 2-methoxy-3-methylpenyl. Similarly, a $C_{1-4}$alkoxy$C_{1-4}$alkyl group means a group resulting from the replacement of one or more hydrogen atoms from a $C_{1-4}$alkyl group with one or more $C_{1-4}$alkoxy groups as defined above, and is a subgroup of the $C_{1-4}$alkoxy$C_{1-6}$alkyl group. Examples of $C_{1-4}$alkoxy$C_{1-4}$alkyl include, among others, methoxymethyl, ethoxymethyl, propoxymethyl, isopropoxymethyl, butoxymethyl, isobutoxymethyl, sec-butoxymethyl, tert-butoxymethyl, dimethoxymethyl, 1-methoxyethyl, 2-methoxyethyl, 2-ethoxyethyl, 1,2-diethoxyethyl, 1-butoxyethyl, 2-sec-butoxyethyl, 3-methoxypropyl, 2-butoxypropyl, 1-methoxy-2-ethoxypropyl, 3-tert-butoxypropyl and 4-methoxybutyl.

A $C_{3-6}$cycloalkyl group, as a group or as a part of a group, means a non-aromatic, monocyclic, hydrocarbon ring group comprising 3 to 6 carbon atoms, which can be optionally substituted by one or more substituents independently selected from $C_{1-4}$alkyl, $C_1$-4alcoxy and halogen, i.e., one or more hydrogen atoms of the ring can be replaced by a $C_{1-4}$alkyl, a $C_1$-4alcoxy or a halogen. When there is more than one substitution, the substituents can be the same or different. Examples of $C_{3-6}$cycloalkyl groups include, for example, cyclopropyl, cyclobutyl, cyclopentyl and cyclohexyl.

A $C_{3-6}$cycloalkyl$C_{1-4}$alkyl group means a group resulting from the replacement of one hydrogen atom from a $C_{1-4}$alkyl group with one $C_{3-6}$cycloalkyl group, as defined above. Examples include, among others, cyclopropylmethyl, cyclobutylmethyl, cyclopentylmethyl, cyclohexylmethyl, cyclopropylethyl, 2-cyclopropylpropyl, 3-cyclopentylpropyl and 4-cyclopentylbutan-2-yl.

The term $C_0$alkyl indicates that the alkyl group is absent.

Thus the term $C_{3-6}$cycloalkyl$C_{0-4}$alkyl includes $C_{3-6}$cycloalkyl and $C_{3-6}$cycloalkyl$C_{1-4}$alkyl as defined above.

The Ph term means a phenyl group which can be optionally substituted by one or more substituents independently selected from $C_{1-4}$alkyl, $C_{1-4}$alcoxy and halogen, i.e., one or more hydrogen atoms of the phenyl group can be replaced by a $C_{1-4}$alkyl, a $C_{1-4}$alcoxy or a halogen. When there is more than one substitution, the substituents can be the same or different.

A Ph$C_{1-4}$alkyl group means a group resulting from the replacement of one hydrogen atom from a $C_{1-4}$alkyl group with one Ph group, as defined above.

Examples include, among others, benzyl, 2-phenylethyl, 3-phenylpropyl and 2-phenylpropyl.

A —$C_{1-4}$alkyl-CONR$_{12}$R$_{13}$ group means a group resulting from the replacement of one hydrogen atom from a $C_{1-4}$alkyl group with one —CONR$_{12}$R$_{13}$ group.

Thorough the description of the current invention, it is understood that when any variable (e.g. $C_{1-6}$alkyl, $C_{1-4}$alkyl, $C_{1-4}$alcoxy, etc.) occurs more than once in a compound of formula (I), its definition on each occurrence is independent of its definition at every each other occurrence, so that the variable may be the same or different on each occasion.

Likewise, when a variable group, such as $R_{12}$ or $R_{13}$, occurs more than once in a compound of formula (I), its definition on each occurrence is independent of its definition at every each other occurrence, so that the variable group is independently selected from its possible meanings at each occurrence, and may have the same meaning or different meaning on each occasion. It may be indicated by the expression "each independently selected from".

Similarly, the term "independently selected from" applied to the definition of a group of different variable groups (e.g. $R_9$, $R_{10}$ and $R_{11}$), means that the definition of each variable of that group is independently selected from the definition of the other variable of the same group, and may have the same meaning or different meanings.

Compounds of the Invention

Also included within the scope of the invention are the pharmaceutically acceptable salts, solvates, isotopes and polymorphs of compounds of formula (I). Thus, any reference to a compound of formula (I) throughout the present specification includes a reference to any pharmaceutically acceptable salt, solvate, isotope or polymorph of such compound of formula (I).

The compounds of the present invention contain basic nitrogen atoms and may, therefore, form salts with organic or inorganic acids. The term "pharmaceutically acceptable salts" as used herein encompasses any salt with no limitation on the type of salt that can be used, provided that these are acceptable for administration to a patient, meaning that they do not induce undue toxicity, irritation, allergic responses, or the like. Pharmaceutically acceptable salts are well known in the art.

For example, the pharmaceutically acceptable salts suitable for being used in the present invention include those derived from the following acids: hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic and tartaric acids, and the like.

The salts of a compound of formula (I) can be obtained, for example, during the final isolation and purification of the compounds of the invention, or can be prepared by treating a compound of formula (I) with a sufficient amount of the desired acid to give the salt in the conventional manner.

The term "solvates" as used herein encompasses a combination of a compound of formula (I) with solvent molecules, bonded by a non-covalent bond. Well known solvent molecules which are able to form solvates include water, alcohols and other polar organic solvents. When the solvate is formed with water, it is also known as a hydrate.

The term "isotopes" as used herein encompasses any isotopically-labeled form of the compounds of formula (I), wherein one or more atoms are replaced by an atom having the same atomic number, but an atomic mass or mass number different from the atomic mass or mass number usually found in nature. Examples of isotopes that can be incorporated into compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulfur, such as $^{35}$S. Those isotopically-labeled compounds are useful, for example, in metabolic or kinetic studies, particularly those labeled with $^2$H, $^3$H, and $^{14}$C. Moreover, substitution with heavier isotopes such as deuterium, $^2$H, may afford certain therapeutic advantages resulting from greater metabolic stability, for example, increased in vivo half-life or reduced dosage requirements.

Isotopically-labeled compounds of the invention can generally be prepared by processes analogous to those described herein, by using an appropriate isotopically-labeled reagent in place of the non-labeled reagent otherwise employed.

The compounds of formula (I) may exist in different physical forms, i.e. amorphous and crystalline forms. Moreover, the compounds of the invention may have the ability to crystallize in more than one form, a characteristic which is known as polymorphism. Polymorphic forms can be distinguished by various physical properties well known in the art such as X-ray diffraction pattern, melting point or solubility. All such physical forms of the compounds of formula (I), including all polymorphic forms ("polymorphs") are included within the scope of the invention.

Furthermore, any formula given herein is also intended to represent the corresponding tautomeric forms. "Tautomer" refers to alternate forms of a molecule that differ in the position of a proton. Examples include, among others, amide-imidic acid form or the amine-imine forms.

The first aspect of the invention is further defined by some specific and preferred embodiments as disclosed below.

In an embodiment, the invention relates to the compounds of formula (I) wherein A is $A_1$.

In another embodiment, the invention relates to the compounds of formula (I) wherein A is $A_2$.

In another embodiment, the invention relates to the compounds of formula (I) wherein A is $A_3$.

In another embodiment, the invention relates to the compounds of formula (I) wherein A is $A_4$.

In another embodiment, the invention relates to the compounds of formula (I) wherein $R_1$ and $R_2$ are independently selected from hydrogen and $C_{1-4}$alkyl, preferably from hydrogen and methyl.

In another embodiment, the invention relates to the compounds of formula (I) wherein $R_1$ and $R_2$ are hydrogen.

In another embodiment, the invention relates to the compounds of formula (I) wherein one of $R_1$ and $R_2$ is hydrogen and the other is $C_{1-4}$alkyl, preferably is methyl.

In another embodiment, the invention relates to the compounds of formula (I) wherein $R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl.

In another embodiment, the invention relates to the compounds of formula (I) wherein $R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy; and more preferably from hydrogen, halogen, methyl and methoxy.

In another embodiment, the invention relates to the compounds of formula (I) wherein $R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine; and $R_3$, $R_4$, $R_6$ and $R_7$ are independently selected from hydrogen and halogen; preferably from hydrogen and fluorine, more preferably $R_3$, $R_4$, $R_6$ and $R_7$ are hydrogen.

In another embodiment, the invention relates to the compounds of formula (I) wherein $R_8$ is selected from wherein $R_8$ is selected from $C_{1-4}$alkyl, $C_{2-4}$alkynyl, halo$C_{1-4}$alkyl, $C_{1-4}$alkoxy$C_{1-4}$alkyl, $C_{3-6}$cycloalkyl$C_{1-4}$alkyl, Ph$C_{1-4}$alkyl and —$C_{1-4}$alkyl-CONR$_{12}$R$_{13}$; more preferably, wherein $R_8$ is selected from $C_{1-6}$alkyl, $C_{2-6}$alkenyl, $C_{2-6}$alkynyl, halo $C_{1-6}$alkyl, hydroxy$C_{1-4}$alkyl, $C_{1-4}$alkoxy, $C_{1-4}$alkoxy $C_{1-4}$alkyl, $C_{3-6}$cycloalkyl$C_{1-4}$alkyl and Ph$C_{1-4}$alkyl; still more preferably wherein $R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl.

In another embodiment, the invention relates to the compounds of formula (I) wherein $R_9$, $R_{10}$ and $R_{11}$ are independently selected from hydrogen, $C_{1-4}$alkyl and $C_{1-4}$alkoxy; more preferably wherein $R_9$, $R_{10}$ and $R_{11}$ are independently selected from hydrogen and $C_{1-4}$alkoxy; still more preferably $R_9$, $R_{10}$ and $R_{11}$ are hydrogen.

In a preferred embodiment, the invention relates to the compounds of formula (I) wherein:

A is $A_1$;

$R_1$ and $R_2$ are independently selected from hydrogen and $C_{1-4}$alkyl; preferably $R_1$ and $R_2$ are independently selected from hydrogen and methyl; more preferably $R_1$ and $R_2$ are hydrogen;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl, Ph$C_{1-4}$alkyl and —$C_{1-4}$alkyl-CONR$_{12}$R$_{13}$; preferably $R_8$ is selected from $C_{1-4}$alkyl, $C_{2-4}$alkynyl, halo$C_{1-4}$alkyl, $C_{3-6}$cycloalkyl$C_{1-4}$alkyl, Ph $C_{1-4}$alkyl;

$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen; and $R_{12}$ and $R_{13}$ are independently selected from hydrogen and from $C_{1-4}$alkyl, preferably from hydrogen and methyl, more preferably $R_{12}$ and $R_{13}$ are both hydrogen or both methyl.

In a preferred embodiment, the invention relates to the compounds of formula (I) wherein:

A is $A_1$;

$R_1$ and $R_2$ are independently selected from hydrogen and $C_{1-4}$alkyl;

$R_3$, $R_4$, $R_5$, $R_6$ and $R_7$ are independently selected from hydrogen, halogen, —OH, $C_{1-6}$alkyl and $C_{1-4}$alkoxy;

$R_8$ is selected from $C_{1-4}$alkyl, $C_{2-4}$alkynyl, halo$C_{1-4}$alkyl, $C_{3-6}$cycloalkyl$C_{1-4}$alkyl, Ph$C_{1-4}$alkyl and —$C_{1-4}$alkyl-CONR$_{12}$R$_{13}$;

$R_9$, $R_{10}$ and $R_{11}$ are independently selected from hydrogen, $C_{1-4}$alkyl and $C_{1-4}$alkoxy; and $R_{12}$ and $R_{13}$ are independently selected from hydrogen and from $C_{1-4}$alkyl.

In a preferred embodiment, the invention relates to the compounds of formula (I) wherein:

A is $A_1$;

$R_1$ and $R_2$ are independently selected from hydrogen and methyl;

$R_3$, $R_4$, $R_5$, $R_6$ and $R_7$ are independently selected from hydrogen, halogen, methyl and methoxy;

$R_8$ is selected from methyl, ethyl, fluromethyl, trifluoroethyl (such as 2,2,2-trifluoroethyl), propynyl, methoxymethyl, benzyl, cyclopropylmethyl, —CH$_2$—CONH$_2$ and —CH$_2$—CO(CH$_3$)$_2$; and $R_9$, $R_{10}$ and $R_{11}$ are independently selected from hydrogen, and methoxy.

In a preferred embodiment, the invention relates to the compounds of formula (I) wherein:

A is $A_1$;

$R_1$ and $R_2$ are hydrogen;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_1$;
$R_1$, $R_2$, $R_3$, $R_4$, $R_6$ and $R_7$ are hydrogen;
$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_1$;
one of $R_1$ and $R_2$ is hydrogen and the other is $C_{1-4}$alkyl, preferably is methyl;
$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_1$;
one of $R_1$ and $R_2$ is hydrogen and the other is $C_{1-4}$alkyl, preferably is methyl;
$R_3$, $R_4$, $R_6$ and $R_7$ are hydrogen;
$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_1$;
$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;
$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_1$;
$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;
$R_3$, $R_4$, $R_6$ and $R_7$ are hydrogen;
$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_2$;
$R_1$ and $R_2$ are hydrogen;
$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_2$;
$R_1$, $R_2$, $R_3$, $R_4$, $R_6$ and $R_7$ are hydrogen;
$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_2$;
one of $R_1$ and $R_2$ is hydrogen and the other is $C_{1-4}$alkyl, preferably is methyl;
$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:
A is $A_2$;
one of $R_1$ and $R_2$ is hydrogen and the other is $C_{1-4}$alkyl, preferably is methyl;
$R_3$, $R_4$, $R_6$ and $R_7$ are hydrogen;
$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;
$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and
$R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_2$;

$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_2$;

$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;

$R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_2$;

$R_1$, $R_2$, $R_3$, $R_4$, $R_6$ and $R_7$ are hydrogen;

$R_5$ is halogen, preferably fluorine;

$R_8$ is $C_{1-4}$alkyl, preferably methyl; and $R_9$, $R_{10}$ and $R_{11}$ are hydrogen.

In a preferred embodiment, the invention relates to the compounds of formula (I) wherein:

A is $A_3$;

$R_1$ and $R_2$ are hydrogen;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_3$;

$R_1$, $R_2$, $R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_3$;

one of $R_1$ and $R_2$ is hydrogen and the other is $C_{1-4}$alkyl, preferably is methyl;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_3$;

one of $R_1$ and $R_2$ is hydrogen and the other is $C_{1-4}$alkyl, preferably is methyl;

$R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_3$;

$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_3$;

$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;

$R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_3$;

$R_1$, $R_2$, $R_3$, $R_4$, $R_6$ and $R_7$ are hydrogen;

$R_5$ is halogen, preferably fluorine;

$R_8$ is $C_{1-4}$alkyl, preferably methyl; and $R_9$, $R_{10}$ and $R_{11}$ are hydrogen.

In a preferred embodiment, the invention relates to the compounds of formula (I) wherein:

A is $A_4$;

$R_1$ and $R_2$ are hydrogen;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_4$;

$R_1$, $R_2$, $R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_4$;

one of $R_1$ and $R_2$ is hydrogen and the other is $C_{1-4}$alkyl, preferably is methyl;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_4$;

one of $R_1$ and $R_2$ is hydrogen and the other is $C_{1-4}$alkyl, preferably is methyl;

$R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_4$;

$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;

$R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy, and more preferably from hydrogen, halogen, methyl and methoxy;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_4$;

$R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl;

$R_3$, $R_4$, $R_6$ and $R_7$ are hydrogen;

$R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine;

$R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl; and $R_9$, $R_{10}$ and $R_{11}$ are independently selected from hydrogen, $C_{1-4}$alkyl and $C_{1-4}$alkoxy, preferably $R_9$, $R_{10}$ and $R_{11}$ are hydrogen.

In a preferred embodiment, the invention relates to the compounds of formula (I) wherein:

A is $A_4$;

$R_1$, $R_2$, $R_3$, $R_4$, $R_6$ and $R_7$ are hydrogen;

$R_5$ is halogen, preferably fluorine;

$R_8$ is $C_{1-4}$alkyl, preferably methyl or ethyl; and $R_9$, $R_{10}$ and $R_{11}$ are hydrogen.

Furthermore, the present invention covers all possible combinations of the particular and preferred embodiments described above.

The first aspect of the invention also relates to the following embodiments:

1.—A compound of formula (I) wherein A is $A_1$.
2.—A compound of formula (I) wherein A is $A_2$.
3.—A compound of formula (I) wherein A is $A_3$.
4.—A compound of formula (I) wherein A is $A_4$.
5.—A compound of formula (I) wherein A is selected from $A_1$, $A_2$ and $A_3$.
6.—A compound of formula (I) wherein A is selected from $A_1$, $A_3$ and $A_4$.
7.—A compound of formula (I) wherein A is selected from $A_2$, $A_3$ and $A_4$.
8.—A compound of formula (I) wherein A is selected from $A_1$, $A_2$ and $A_4$.
9.—A compound of formula (I) wherein A is selected from $A_1$ and $A_2$.
10.—A compound of formula (I) wherein A is selected from $A_1$ and $A_3$.
11.—A compound of formula (I) wherein A is selected from $A_1$ and $A_4$.
12.—A compound of formula (I) wherein A is selected from $A_2$ and $A_3$.
13.—A compound of formula (I) wherein A is selected from $A_2$ and $A_4$.
14.—A compound of formula (I) wherein A is selected from $A_3$ and $A_4$.
15.—A compound according to any of embodiments 1 to 14, wherein $R_1$ and $R_2$ are independently selected from hydrogen and $C_{1-4}$alkyl, preferably from hydrogen and methyl.

16.—A compound according to embodiment 15, wherein $R_1$ and $R_2$ are hydrogen.

17.—A compound according to embodiment 15, wherein one of $R_1$ and $R_2$ is hydrogen and the other is $C_{1-4}$alkyl, preferably is methyl.

18.—A compound according to embodiment 15, wherein $R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl.

19.—A compound according to any of embodiments 1 to 18, wherein $R_3$, $R_4$, $R_5$, $R_6$ and $R_7$ are independently selected from hydrogen, halogen, —OH, $C_{1-6}$alkyl and $C_{1-4}$alkoxy; preferably from hydrogen, halogen, $C_{1-4}$alkyl and $C_{1-4}$alkoxy; and more preferably from hydrogen, halogen, methyl and methoxy.

20.—A compound according to embodiment 19, wherein $R_5$ is selected from halogen, —OH, $C_{1-6}$alkyl and $C_{1-4}$alkoxy; preferably from halogen, $C_{1-4}$alkyl and $C_{1-4}$alkoxy; more preferably from halogen, methyl and methoxy; and still more preferably $R_5$ is fluorine; and $R_3$, $R_4$, $R_6$ and $R_7$ are hydrogen.

21.—A compound according to any of embodiments 1 to 20, wherein $R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl.

22.—A compound according to any of embodiments 1 to 21, wherein $R_9$, $R_{10}$ and $R_{11}$ are independently selected from hydrogen, $C_{1-4}$alkyl and $C_{1-4}$alkoxy.

23.—A compound according to embodiment 22, wherein $R_9$, $R_{10}$ and $R_{11}$ are hydrogen.

As disclosed above, in the first aspect of the present invention, the following compounds are excluded from all the specific embodiments herein described, in particular from any of embodiments 1 to 23 herein described where they are encompassed:

1-benzyl-2-oxo-1,2-dihydro-pyridine-3-carboxylic acid N'-(2-(trifluoromethyl)phenyl)-hydrazide, 1-benzyl-4,6-dimethyl-2-oxo-1,2-dihydro-pyridine-3-carboxylic acid N'-phenyl-hydrazide, 1-methyl-2-oxo-1,2-dihydro-pyridine-4-carboxylic acid N'-(2,4,6-trichlorophenyl)-hydrazide, 1-((3-methylphenyl)methyl)-2-oxo-1,2-dihydro-pyridine-3-carboxylic acid N'-(3-(trifluoromethyl)phenyl)-hydrazide, and 1-((2-chlorophenyl)methyl)-6-oxo-1,6-dihydro-pyridine-3-carboxylic acid N'-phenyl-N'-methyl-hydrazide.

In a preferred embodiment, compound of formula (I) is selected from the following list of compounds:

1-methyl-6-oxo-1,6-dihydropyridine-2-carboxylic acid, N'-(4-fluorophenyl)-hydrazide;

1-ethyl-6-oxo-1,6-dihydropyridine-2-carboxylic acid, N'-(4-fluorophenyl)-hydrazide;

1-(2-methoxyethyl)-6-oxo-1,6-dihydropyridine-2-carboxylic acid, N'-(4-fluorophenyl)-hydrazide;

1-difluoromethyl-6-oxo-1,6-dihydropyridine-2-carboxylic acid, N'-(4-fluorophenyl)-hydrazide;

1-benzyl-6-oxo-1,6-dihydropyridine-2-carboxylic acid, N'-(4-fluorophenyl)-hydrazide;

1-cyclopropylmethyl-6-oxo-1,6-dihydropyridine-2-carboxylic acid, N'-(4-fluorophenyl)-hydrazide;

4-methoxy-1-methyl-6-oxo-1,6-dihydropyridine-2-carboxylic acid, N'-(4-fluorophenyl)-hydrazide;

1-(prop-2-yn-1-yl)-6-oxo-1,6-dihydropyridine-2-carboxylic acid, N'-(4-fluorophenyl)-hydrazide;

5-ethyl-1-methyl-6-oxo-1,6-dihydropyridine-2-carboxylic acid, N'-(4-fluorophenyl)-hydrazide; 6-oxo-1-(2,2,2-trifluoroethyl)-1,6-dihydropyridine-2-carboxylic acid, N'-(4-fluorophenyl)-hydrazide;

1-methyl-6-oxo-1,6-dihydropyridine-2-carboxylic acid, N'-(4-methoxyphenyl)-hydrazide;

1-methyl-6-oxo-1,6-dihydropyridine-2-carboxylic acid, N'-(4-chlorophenyl)-hydrazide;

1-methyl-6-oxo-1,6-dihydropyridine-2-carboxylic acid, N'-(4-methylphenyl)-hydrazide;

1-methyl-6-oxo-1,6-dihydropyridine-2-carboxylic acid, N'-(2,4-difluorophenyl)-hydrazide;

1-methyl-6-oxo-1,6-dihydropyridine-2-carboxylic acid, N'-(2,6-difluorophenyl)-hydrazide;

1-methyl-6-oxo-1,6-dihydropyridine-2-carboxylic acid, N'-(4-fluorophenyl)-N,N'-dimethyl-hydrazide;

1-methyl-6-oxo-1,6-dihydropyridine-2-carboxylic acid, N'-(4-fluorophenyl)-N'-methyl-hydrazide;

1-methyl-6-oxo-1,6-dihydropyridine-2-carboxylic acid, N'-(4-fluorophenyl)-N-methyl-hydrazide; 1-(2-(dimethylamino)-2-oxoethyl)-6-oxo-1,6-dihydropyridine-2-carboxylic acid, N'-(4-fluorophenyl)-hydrazide;

1-(2-amino-2-oxoethyl)-6-oxo-1,6-dihydropyridine-2-carboxylic acid, N'-(4-fluorophenyl)-hydrazide;

1-ethyl-2-oxo-1,2-dihydropyridine-3-carboxylic acid, N'-(4-fluorophenyl)-hydrazide;

1-methyl-2-oxo-1,2-dihydropyridine-3-carboxylic acid, N'-(4-fluorophenyl)-hydrazide;

1-methyl-2-oxo-1,2-dihydropyridine-4-carboxylic acid, N'-(4-fluorophenyl)-hydrazide; and 1-methyl-6-oxo-1,6-dihydropyridine-3-carboxylic acid, N'-(4-fluorophenyl)-hydrazide;

and the pharmaceutically acceptable salts or solvates thereof.

In another embodiment, the invention relates to compounds of formula (I) having a minimal inhibitory concentration (MIC) against *Acinetobacter baumannii* of less than about 8 µg/mL, more preferably of less than about 4 µg/mL, and still more preferably of less than about 2 µg/mL, in an assay as the one described in Example 22.

In another embodiment, the invention relates to compounds of formula (I) having (a) a MIC against *Acinetobacter baumannii* of less than about 8 µg/mL, more preferably of less than about 4 µg/mL, and still more preferably of less than about 2 µg/mL; and (b) a MIC greater than about 100 µg/mL against at least one of the following bacteria: *Staphylococcus aureus, Streptococcus pneumoniae, Enterococcus faecium, Pseudomonas aeruginosa, Klebsiella pneumoniae, Enterobacter aerogenes* and *Escherichia coli*, preferably against at least two of these bacteria, and still more preferably against at least three of these bacteria; in an assay as the one described in Example 22.

Use of the Compounds

As shown in Example 22, surprisingly, the compounds of the present invention showed high antimicrobial activity against the bacteria *A. baumannii*, with minimal inhibitory concentration (MIC) values equal to or less than 1 µg/mL for almost all the assayed compounds, while they were inactive against the other bacteria tested, i.e. *S. aureus, S. pneumoniae, E. faecium, P. aeruginosa, K. pneumoniae, E. aerogenes* and *E. coli*, with MIC values greater than 128 for almost all the compounds.

Therefore, another aspect of the present invention is a compound of formula (I):

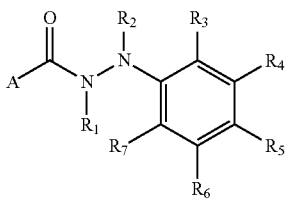

or a pharmaceutically acceptable salt, or solvate thereof, wherein

A is a radical selected from $A_1$, $A_2$, $A_3$ and $A_4$;

$A_1$ is

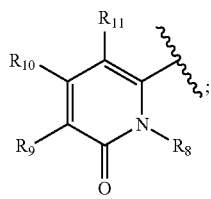

$A_2$ is

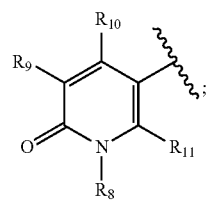

$A_3$ is

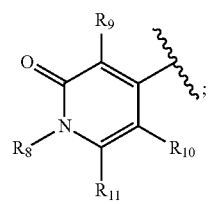

$A_4$ is

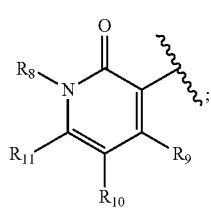

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$;

$R_8$ is selected from $C_{1-6}$alkyl, $C_{2-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl, Ph $C_{1-4}$alkyl and —$C_{1-4}$alkyl-$CONR_{12}R_{13}$;

$R_9$, $R_{10}$ and $R_{11}$ are independently selected from hydrogen, $C_{1-6}$alkyl, $C_{3-6}$cycloalkyl$C_{1-4}$alkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$; and each $R_{12}$ and $R_{13}$ are independently selected from hydrogen and $C_{1-4}$alkyl;

for use as a medicament.

Another aspect of the present invention is a compound of formula (I):

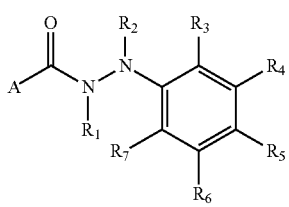

or a pharmaceutically acceptable salt, or solvate thereof, wherein

A is a radical selected from $A_1$, $A_2$, $A_3$ and $A_4$;

$A_1$ is

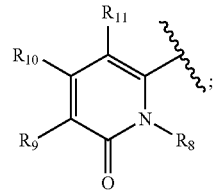

$A_2$ is

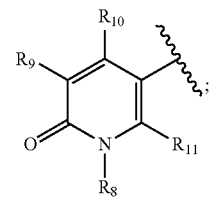

$A_3$ is

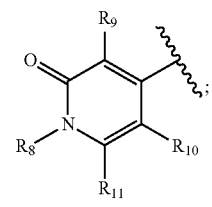

$A_4$ is

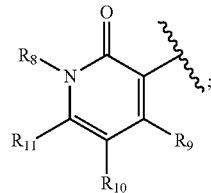

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —$NR_{12}R_{13}$, —$N(R_{12})COR_{13}$, —$N(R_{12})SO_2R_{13}$, halo $C_{1-6}$alkyl, hydroxy$C_{1-6}$alkyl, $C_{1-4}$alkoxy, $C_{1-4}$alkoxy $C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$;

$R_8$ is selected from $C_{1-6}$alkyl, $C_{2-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl, Ph $C_{1-4}$alkyl and —$C_{1-4}$alkyl-$CONR_{12}R_{13}$;

$R_9$, $R_{10}$ and $R_{11}$ are independently selected from hydrogen, $C_{1-6}$alkyl, $C_{3-6}$cycloalkyl$C_{1-4}$alkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$; and each $R_{12}$ and $R_{13}$ are independently selected from hydrogen and $C_{1-4}$alkyl;

for use as antibacterial agent, preferably for treating or preventing A. baumannii infections.

Particular embodiments are directed to the compound of formula (I) for use as defined above, wherein A, $R_1$, $R_2$, $R_3$, $R_4$, $R_5$, $R_6$, $R_7$, $R_8$, $R_9$, Rio, $R_{11}$, $R_{12}$ and $R_{13}$ are as previously defined with respect to the compound of formula (I), or wherein the compound of formula (I) is a particular compound mentioned above, i.e., a compound selected from the group consisting of:

1-methyl-6-oxo-1,6-dihydropyridine-2-carboxylic acid, N'-(4-fluorophenyl)-hydrazide;
1-ethyl-6-oxo-1,6-dihydropyridine-2-carboxylic acid, N'-(4-fluorophenyl)-hydrazide;
1-(2-methoxyethyl)-6-oxo-1,6-dihydropyridine-2-carboxylic acid, N'-(4-fluorophenyl)-hydrazide;
1-difluoromethyl-6-oxo-1,6-dihydropyridine-2-carboxylic acid, N'-(4-fluorophenyl)-hydrazide;
1-benzyl-6-oxo-1,6-dihydropyridine-2-carboxylic acid, N'-(4-fluorophenyl)-hydrazide;
1-cyclopropylmethyl-6-oxo-1,6-dihydropyridine-2-carboxylic acid, N'-(4-fluorophenyl)-hydrazide;
4-methoxy-1-methyl-6-oxo-1,6-dihydropyridine-2-carboxylic acid, N'-(4-fluorophenyl)-hydrazide;
1-(prop-2-yn-1-yl)-6-oxo-1,6-dihydropyridine-2-carboxylic acid, N'-(4-fluorophenyl)-hydrazide;
5-ethyl-1-methyl-6-oxo-1,6-dihydropyridine-2-carboxylic acid, N'-(4-fluorophenyl)-hydrazide;
6-oxo-1-(2,2,2-trifluoroethyl)-1,6-dihydropyridine-2-carboxylic acid, N'-(4-fluorophenyl)-hydrazide;
1-methyl-6-oxo-1,6-dihydropyridine-2-carboxylic acid, N'-(4-methoxyphenyl)-hydrazide;
1-methyl-6-oxo-1,6-dihydropyridine-2-carboxylic acid, N'-(4-chlorophenyl)-hydrazide;
1-methyl-6-oxo-1,6-dihydropyridine-2-carboxylic acid, N'-(4-methylphenyl)-hydrazide;
1-methyl-6-oxo-1,6-dihydropyridine-2-carboxylic acid, N'-(2,4-difluorophenyl)-hydrazide;
1-methyl-6-oxo-1,6-dihydropyridine-2-carboxylic acid, N'-(2,6-difluorophenyl)-hydrazide;
1-methyl-6-oxo-1,6-dihydropyridine-2-carboxylic acid, N'-(4-fluorophenyl)-N,N'-dimethyl-hydrazide;
1-methyl-6-oxo-1,6-dihydropyridine-2-carboxylic acid, N'-(4-fluorophenyl)-N'-methyl-hydrazide;
1-methyl-6-oxo-1,6-dihydropyridine-2-carboxylic acid, N'-(4-fluorophenyl)-N-methyl-hydrazide;
1-(2-(dimethylamino)-2-oxoethyl)-6-oxo-1,6-dihydropyridine-2-carboxylic acid, N'-(4-fluorophenyl)-hydrazide;
1-(2-amino-2-oxoethyl)-6-oxo-1,6-dihydropyridine-2-carboxylic acid, N'-(4-fluorophenyl)-hydrazide;
1-ethyl-2-oxo-1,2-dihydropyridine-3-carboxylic acid, N'-(4-fluorophenyl)-hydrazide;
1-methyl-2-oxo-1,2-dihydropyridine-3-carboxylic acid, N'-(4-fluorophenyl)-hydrazide;
1-methyl-2-oxo-1,2-dihydropyridine-4-carboxylic acid, N'-(4-fluorophenyl)-hydrazide; and
1-methyl-6-oxo-1,6-dihydropyridine-3-carboxylic acid, N'-(4-fluorophenyl)-hydrazide;

or a pharmaceutically acceptable salt, or solvate thereof.

A preferred embodiment relates to any of the particular and preferred embodiments of compounds formula (I) above disclosed in relation with the first aspect of the present invention for use as antibacterial agents, preferably for treating or preventing A. baumannii infections.

This aspect of the present invention can be similarly reformulated according to the following aspects.

Thus, another aspect of the present invention relates to a method for treating a bacterial infections in a subject in need thereof, comprising administering an effective amount of a compound of formula (I) as defined above, or a pharmaceutically acceptable salt or solvate thereof, to the subject.

Another aspect of the present invention relates to the use of a compound of formula (I) as defined above, or a pharmaceutically acceptable salt or solvate thereof, as antibacterial agent.

Another aspect of the present invention relates to a method for treating a A. baumannii infection in a subject in need thereof, comprising administering an effective amount of a compound of formula (I) as defined above, or a pharmaceutically acceptable salt or solvate thereof, to the subject.

Still another aspect of the present invention relates to the use of a compound of formula (I) as defined above, or a pharmaceutically acceptable salt or solvate thereof, for treating A. baumannii infections.

The compounds of the present invention may be used without limitation for the treatment of all infections caused by A. baumannii. For example, they can be used for treating pneumonia, particularly ventilator-associated pneumonia; surgical site infections; wound infections; skin and soft tissue infections; urinary tract infections; post-operative meningitis; any kind of catheter-related infection, for example catheter-associated urinary tract infection; or bloodstream infection.

As used herein the terms "treatment" or "treating" refer to both prophylactic treatment and therapeutic treatment of A. baumannii infections i.e. to preventing or inhibiting the infection from occurring in a subject that may be predisposed to be infected but has not yet been diagnosed as having the infection, and to reducing or eliminating the infection after its onset in a subject, as well as to relieving and alleviating its associated symptoms.

Particularly, the terms "prevention" or "preventing" refer more specifically to prophylactic treatment of *A. baumannii* infections i.e. to preventing or inhibiting the infection from occurring in a subject that may be predisposed to be infected but has not yet been diagnosed as having the infection.

As used herein the term "subject" is referred to human beings. As used herein the term "in a subject in need thereof" relates to both a subject who has not been infected but that may be predisposed to acquire the infection as well as to a subject who has been infected with *A. baumannii*.

The compounds of the present invention are administered in a dose which is therapeutically active for treating the infections, and the skilled in the art will have no difficulty for adjusting the exact dose to be administered based on the kind of patient, the specific infection to be treated and its severity.

Typically, the compounds of the invention are administered in an amount ranging from 1 to 20 mg/kg of body weight.

Pharmaceutical Compositions

Another aspect of the invention relates to a pharmaceutical composition which comprises a compound of formula (I) or a pharmaceutical acceptable salt or solvate thereof, as previously defined, and at least one pharmaceutically acceptable excipient and/or carrier.

The pharmaceutical composition that is an aspect of the present invention can be adapted to any form of administration, for example for oral, parenteral, by inhalation, rectal, transdermal or topical administration. Likewise, depending on the intended route, the composition may be in solid, liquid, or semi-solid form, and all of them are encompassed within the scope of the present invention.

The excipients suitable to be used in the pharmaceutical composition as well as their preparation methods will vary depending on the form and intended route of administration.

Solid compositions for oral use include, for example, tablets, capsules, and granulates. They may contain excipients such, for example, anticaking agents, binders, diluents, disintegrating agents, glidants, lubricants, flavoring agents and sweetening agents. Tablets can be coated with diverse coating agents. Capsules can be either hard capsules or soft capsules as are well known in the art.

Liquid forms for oral administration include emulsions, solutions, suspensions and syrups and can incorporate diverse pharmaceutically acceptable carriers or excipients, such as a liquid vehicle, emulsifying agents, suspending agents, flavoring agents, coloring agents, buffering agents, preservative agents, and diluents.

Injectable preparations comprise sterile solutions, suspensions or emulsions in aqueous or non-aqueous solvents such as propylene glycol, polyethylene glycol or vegetable oils, and can be administered intravenously, subcutaneously or intramuscularly.

Compositions for rectal administration can be in the form of suppositories, for example on an oily base. They may contain other excipients such adsorbents, surface-active agents, antioxidants, preservatives and colorants.

Compositions for topical administration can be in form of creams, gels, ointments or pastes, for example. They may contain excipients such emulsifiers, viscosity-increasing agents, preservatives, antioxidants, and stabilizing agents.

In each case, the pharmaceutical compositions can be prepared using standard methods that are well known to the skilled in the art such as those described in handbooks of pharmaceutical technology, for example the book *Remington The Science and Practice of Pharmacy*, 20$^{th}$ edition, Lippincott, Williams & Wilkins, Philadelphia, 2000 [ISBN: 0-683-306472].

Also the excipients and/or carriers to be used in such compositions are well known, as disclosed for example, in the book R. C. Rowe, P. J. Sheskey and M. E. Quinn, *Handbook of Pharmaceutical Excipients*, 6$^{th}$ edition, Pharmaceutical Press, London, 2009 [ISBN: 978 0 85369 792 3].

Such compositions typically contain from 1 to 40% by weight of compound of formula (I) as active ingredient, the remainder of the composition being pharmaceutical carriers and/or excipients.

Process for Preparing the Compounds of the Invention

The compounds of the invention can be prepared by the methods described herein, o using similar methods. It will be appreciated that while some preferred conditions are herewith disclosed for carrying out the processes, such as temperature, reagents, or solvents, for example, it will be matter of routine for the skilled in the art to adjust such conditions to each particular case to achieve optimized results.

Furthermore, as is well known to the skilled in the art, the use of conventional protecting groups may be necessary to prevent undesired reactions of some reactive or labile groups. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, "*Protecting Groups in Organic Synthesis*", Third Edition, Wiley, New York, 1999, and the references cited therein.

Thus, another aspect of the present invention relates to a process for the preparation of a compound of formula (I) as defined above, or a pharmaceutically acceptable salt or solvate thereof, which comprises reacting a compound of formula (II)

with a compound of formula (III) or a pharmaceutically acceptable salt or solvate thereof:

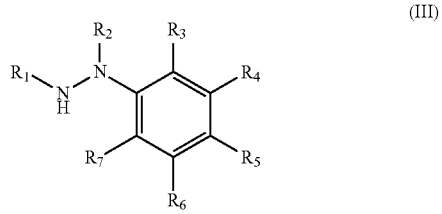

wherein A and $R_1$ to $R_{13}$ have the same meaning as defined above in relation to compounds of formula (I).

Another embodiment relates to a process for the preparation of a compound of formula (I) as defined above, or a pharmaceutically acceptable salt, or solvate thereof, wherein A is $A_1$, which comprises reacting a compound of formula ($II_a$)

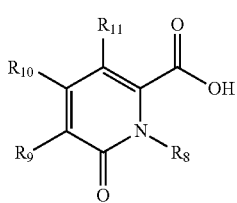

(II$_a$)

with a compound of formula (III) or a pharmaceutically acceptable salt or solvate thereof:

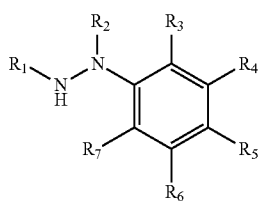

(III)

wherein $R_1$ to $R_{13}$ have the same meaning as defined above in relation to compounds of formula (I).

Another embodiment relates to a process for the preparation of a compound of formula (I) as defined above, or a pharmaceutically acceptable salt or solvate thereof, wherein A is A$_2$, which comprises reacting a compound of formula (II$_b$)

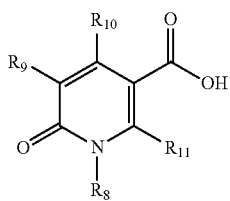

(II$_b$)

with a compound of formula (III) or a pharmaceutically acceptable salt or solvate thereof:

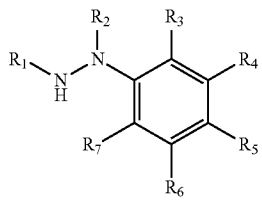

(III)

wherein $R_1$ to $R_{13}$ have the same meaning as defined above in relation to compounds of formula (I).

Another embodiment relates to a process for the preparation of a compound of formula (I) as defined above, or a pharmaceutically acceptable salt, or solvate thereof, wherein A is A$_3$, which comprises reacting a compound of formula (II$_c$)

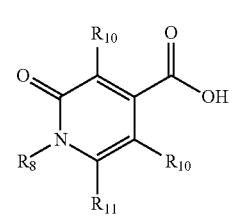

(II$_c$)

with a compound of formula (III) or a pharmaceutically acceptable salt or solvate thereof:

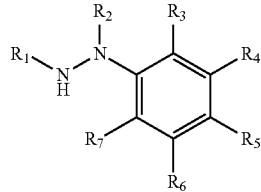

(III)

wherein $R_1$ to $R_{13}$ have the same meaning as defined above in relation to compounds of formula (I).

Another embodiment relates to a process for the preparation of a compound of formula (I) as defined above, or a pharmaceutically acceptable salt or solvate thereof, wherein A is A$_4$, which comprises reacting a compound of formula (II$_d$)

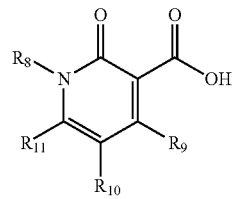

(II$_d$)

with a compound of formula (III) or a pharmaceutically acceptable salt or solvate thereof:

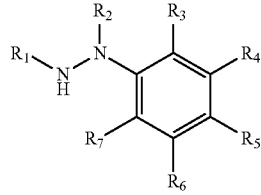

(III)

wherein $R_1$ to $R_{13}$ have the same meaning as defined above in relation to compounds of formula (I).

The coupling reaction, as defined in the previous embodiments, is preferably performed in the presence of a coupling agent, as are well known to the skilled in medicinal chemistry. For example the following coupling agents may be used: ethyl-(N',N'-dimethylamino)propylcarbodiimide hydrochloride (also known as EDCI.HCl), or (1-[bis(dimethylamino)methylene]-1H-1,2,3-triazolo[4,5-b]pyridinium-3-oxid hexafluorophosphate) (also known as HATU).

Compounds (II) and (III) are suitably reacted in the presence of a coupling agent and in the presence of a base. Suitable bases include N,N-diisopropylethylamine (DIPEA), triethylamine (Et$_3$N), 4-dimethylaminopyridine (DMAP), or mixtures thereof.

The coupling reaction can take place in an inert organic solvent. Suitable organic solvents are, for example, aromatic hydrocarbons such as benzene, toluene or xylene; halogenated hydrocarbons such as dichloromethane, chloroform or dichloroethane; ethers, such as tetrahydrofuran, dioxane, diethylether or diisopropyl ether; nitriles such as acetonitrile or propionitrile; ketones such as acetone, methyl ethyl ketone or diethyl ketone; alcohols, such as methanol, ethanol, n-propanol, isopropanol or n-butanol; and also dimethylformamide (DMF) or dimethylsulfoxide (DMSO), or mixtures thereof. A preferred solvent is dichloromethane.

A preferred method for carrying out the coupling of compound (II) (either II$_a$, II$_b$, II$_c$ or II$_d$) with compound (III), as defined above, involves using the coupling agent EDCI·HCl, and a mixture of Et$_3$N and DMAP bases. This reaction can be carried out in dry dichloromethane, at room temperature and under nitrogen atmosphere.

Another preferred method for carrying out this coupling reaction involves using the coupling agent HATU using DIPEA as a base. This reaction can be carried out in dry dichloromethane, at room temperature and under nitrogen atmosphere.

Another preferred method for carrying out this coupling reaction involves using the coupling agent EDCI.HCl, using DIPEA as a base, and 1-hydroxybenzotriazole (HOBt) as a coupling aid. This reaction can be carried out in dry dichloromethane, at room temperature and under nitrogen atmosphere.

Compounds of formula (II) are either commercially available or can be prepared using methods known to the skilled in the art. For example, a suitable method for preparing a compound of formula (II$_a$) from a compound of formula (II$_a$') is depicted in Scheme 1.

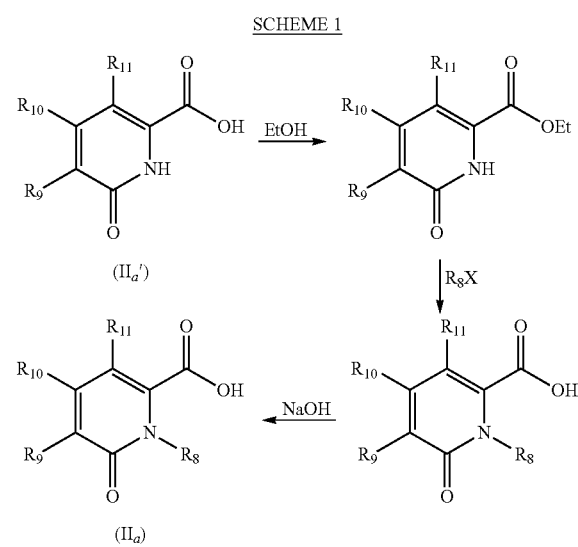

SCHEME 1

Thus, the carboxylic acid group of compound (II$_a$') is first protected in form of an ester (ethyl ester), which is further reacted with compound R$_8$X, wherein X is a leaving group, and subsequently the ethyl ester is hydrolyzed with a base, typically with NaOH, to obtain compound (II$_a$), wherein R$_8$, R$_9$, R$_{10}$ and R$_{11}$ have the same meaning as disclosed above in relation to compounds of formula (I).

Suitable leaving groups are well known in the art, for example, Cl, Br, I, tosylate, or mesylate.

In an analogous way, compounds of formula (II$_b$), (II$_c$) and (II$_d$) can be obtained from the equivalent compounds (II$_b$'), (II$_c$') and (II$_d$'):

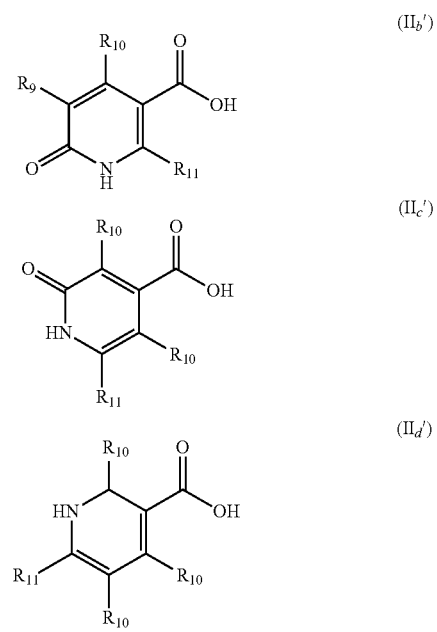

Compounds (II') and (III) are either commercially available or can be obtained by conventional methods known to those skilled in the art.

The following examples are provided by way of illustration and should not be construed as limiting the present invention.

EXAMPLES

General Methods

Moisture and oxygen sensitive reactions were conducted in dry glassware (Schlenk flasks sealed with rubber septa) under nitrogen.

Solvents

All solvents used were of analytical-grade quality and if not otherwise mentioned demineralised water was used.

Water-free solvents were freshly distilled under N$_2$ atmosphere prior to use.
  Tetrahydrofuran (THF) from sodium-benzophenone ketyl,
  Methanol form magnesium methanolate,
  Dichloromethane (CH$_2$Cl$_2$) from calcium hydride.

HPLC solvents were of gradient-grade quality and double distilled water was used. All eluents were degassed by sonication prior to use.

Flash Column Chromatography (Fc)

Flash column chromatography (fc) was conducted with silica gel (100-200 μm) (Spectrochem) as stationary phase. Compressed air was used to push the solvent through the column.

HPLC Method

Model: Waters 2695 Separation Module
Column: Waters XTerra® MS C18 (5 μm) 2.1×250 mm Column
Solvent: A: acetonitrile with 0.05% (v/v) formic acid. B: water with 0.05% (v/v) formic acid
Gradient:

| time [min] | solvent A [%] | solvent B [min] |
|---|---|---|
| 0.0 | 5.0 | 95.0 |
| 3.0 | 5.0 | 95.0 |
| 10.0 | 100.0 | 0.0 |
| 15.0 | 100.0 | 0.0 |
| 17.0 | 5.0 | 95.0 |
| 18.0 | 5.0 | 95.0 |

Flow rate: 0.30 mL/min
Injection: volume: 2.0 μL
Wavelength: 210-240 nm
Baseline auto zero: 0.0 min
Calculation: use blank subtraction from same series
Integration: manual
Calculation method: area %
All HPLC methods were performed at room temperature.

Mass Spectrometry

The mass spectra were recorded with a Micromass Quatro Micro™ API mass spectrometer. As all samples were measured in the positive and negative ion mode, all specified fragments display positively charged ions or radicals. The mass-to-charge ratios m/z and the relative signal intensities [%] of the ions are given.

NMR Spectroscopy $^1$H NMR (500 MHz) and $^{13}$C NMR spectra were recorded on a Brucker UltraShield (500 MHz), operating at 23° C. Chemical shifts δ are reported in parts per million (ppm) against the reference compound tetramethylsilane and calculated using the chemical shift of the signal of the undeuterated solvent.

Abbreviations for the multiplicities of the signals:
s=singlet, d=doublet, t=triplet, q=quartet, quint=quintet, m=multiplet, dd=doublet of doublets etc.

Example 1

1-Methyl-6-oxo-1,6-dihydro-pyridine-2-carboxylic acid N'-(4-fluoro-phenyl)-hydrazide 620 mg (3.7 mmol, 1 equiv.) of 1-methyl-6-oxo-1,6-dihydro-pyridine-2-carboxylic acid were dissolved in 5 mL of dry dichloromethane and to it DIPEA (3 equiv.) and HATU (1 equiv.) were added. After 10 min stirring at 0° C., (4-fluorophenyl)-hydrazine hydrochloride (1.5 equiv.) was added. The reaction mixture was allowed to stir overnight at room temperature under nitrogen atmosphere. After the completion of the reaction, solvent was removed and the residue was washed with brine (two times, 5 mL) and extracted with dichloromethane (three times, 10 mL). The collected organic phase was dried over anhydrous Na$_2$SO$_4$, and concentrated under reduced pressure. The crude product was purified by column chromatography to obtain 200 mg of pure title compound (19%).

$^1$H NMR (500 MHz, CDCl$_3$) δ: 3.4 (s, 3H), 4.39-4.44 (m, 2H), 6.49-6.50 (m, 1H), 6.55-6.57 (m, 1H), 6.82-6.85 (m, 2H), 7.02-7.06 (m, 2H), 7.48-7.50 (m, 1H), 10.62 (s, 1H); Signal of a NH proton was not observed; LC-MS: 262.2 (M+H); Purity (HPLC): 94.44%

Example 2

1-Ethyl-6-oxo-1,6-dihydro-pyridine-2-carboxylic acid N'-(4-fluoro-phenyl)-hydrazide Step 1: 6-Oxo-1, 6-dihydro-pyridine-2-carboxylic acid ethyl ester

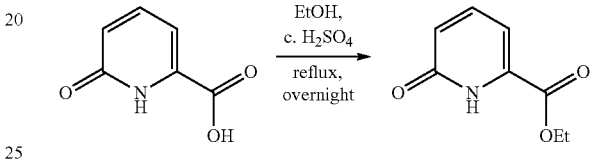

850 mg (6.11 mmol) of 6-oxo-1,6-dihydro-pyridine-2-carboxylic acid was dissolved in 14 mL of dry ethanol and to it 0.75 mL of concentrated H$_2$SO$_4$ was added slowly under ice-cooled conditions. The reaction mixture was allowed to stir overnight at reflux under nitrogen atmosphere. After the completion of reaction, the reaction mixture was concentrated under vacuum. Saturated NaHCO$_3$ solution was added to the reaction mixture until the pH of solution was 8. Then it was extracted with dichloromethane (three times, 15 mL) and the collected organic phase was dried over anhydrous Na$_2$SO$_4$, concentrated under vacuum, yielding 800 mg (78%) of crude title compound. LC-MS: 168.2 (M+H).

Step 2: 1-Ethyl-6-oxo-1, 6-dihydro-pyridine-2-carboxylic acid ethyl ester

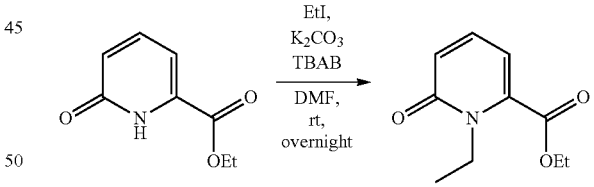

To a stirring solution of 500 mg (2.99 mmol) of 6-oxo-1,6-dihydro-pyridine-2-carboxylic acid ethyl ester obtained step 1, in 6 mL of dry DMF, 1.03 g (7.48 mmol) of K$_2$CO$_3$ and 96.4 mg (0.299 mmol) of tetra n-butylammonium chloride (TBAB) were added. The reaction mixture was allowed to stir for 10 min at room temperature. The reaction mixture was cooled at 0° C. and to it 0.48 mL (5.98 mmol) of ethyl iodide was added. After the completion of reaction, the reaction mixture was quenched with cold water and extracted with ethyl acetate (three times, 15 mL). The collected organic layer was dried over anhydrous Na$_2$SO$_4$ and concentrated under vacuum. The crude reaction mixture was purified by column chromatography (4% ethyl acetate in hexane) to yield 255 mg (44%) of title compound. LC-MS: 196.2 (M+H).

Step 3: 1-Ethyl-6-oxo-1, 6-dihydro-pyridine-2-carboxylic acid

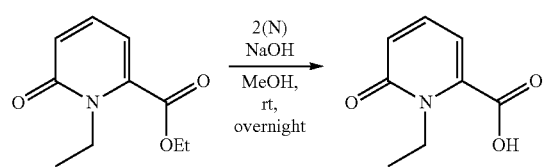

250 mg (1.28 mmol) of 1-ethyl-6-oxo-1,6-dihydro-pyridine-2-carboxylic acid ethyl ester obtained in step 2 was dissolved in 8 mL of methanol and to it 4 mL aqueous 2(N) NaOH solution was added. The reaction mixture was stirred at room temperature overnight. After the completion of reaction, the reaction mixture was concentrated under reduced pressure and to the residue 2(N) HCl solution was added until the pH of the reaction mixture became 2. The resulting mixture was extracted with 10% methanol in dichloromethane. The collected organic layer was dried over anhydrous $Na_2SO_4$ and concentrated under vacuum to yield 126 mg of title compound.

LC-MS: 168.2 (M+H)

Step 4: 1-Ethyl-6-oxo-1,6-dihydro-pyridine-2-carboxylic acid N'-(4-fluorophenyl)-hydrazide

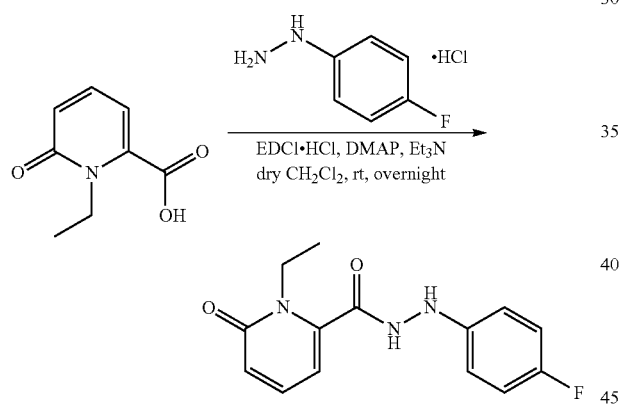

125 mg (0.77 mmol, 1 equiv.) of 1-ethyl-6-oxo-1,6-dihydro-pyridine-2-carboxylic acid obtained in step 3 was dissolved in 7 mL of dry dichloromethane and to it $Et_3N$ (3 equiv.), EDCI.HCl (2 equiv.) and DMAP (1 equiv.) were added. After 10 min stirring at 0° C., (4-fluorophenyl)-hydrazine hydrochloride (1.5 equiv.) was added. The reaction mixture was allowed to stir overnight at room temperature under nitrogen atmosphere. After the completion of the reaction, solvent was removed and the residue was washed with brine (two times, 5 mL) and extracted with dichloromethane (three times, 10 mL). The collected organic phase was dried over anhydrous $Na_2SO_4$, and concentrated under reduced pressure. The crude product was purified by column chromatography to obtain 22 mg of pure title compound (10%).

$^1H$ NMR (500 MHz, $CDCl_3$) δ: 1.44-1.47 (m, 3H), 4.39-4.44 (m, 2H), 6.88-6.91 (m, 2H), 6.93-6.97 (m, 32H), 7.72-7.77 (m, 2H), 9.30 (s, 1H); Signal of a NH proton was not observed; LC-MS: 276.3 (M+H); Purity (HPLC): 94.40%.

Example 3

1-(2-methoxyethyl)-6-oxo-1,6-dihydro-pyridine-2-carboxylic acid N'-(4-fluorophenyl)-hydrazide

Step 1: 1-(2-methoxyethyl)-6-oxo-1,6-dihydro-pyridine-2-carboxylic acid ethyl ester

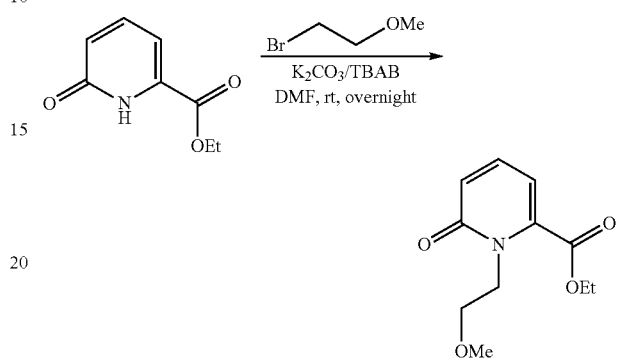

To a stirring solution of 200 mg (1.19 mmol) of 6-oxo-1,6-dihydro-pyridine-2-carboxylic acid ethyl ester (prepared as in Step 1 of Example 1) in 6 mL of dry DMF, 330 mg (2.39 mmol) of $K_2CO_3$ and 39 mg (0.119 mmol) of TBAB were added. The reaction mixture was allowed to stir for 10 min at room temperature. The reaction mixture was cooled at 0° C. and to it 0.22 mL (2.39 mmol) of 1-bromo-2-methoxyethane were added. After the completion of reaction, the reaction mixture was quenched with cold water and extracted with ethyl acetate (three times, 15 mL). The collected organic layer was dried over anhydrous $Na_2SO_4$ and concentrated under vacuum. The crude reaction mixture was purified by column chromatography (4% ethyl acetate in hexane) to yield 65 mg (24%) of title compound. LC-MS: 226.4 (M+H).

Step 2: 1-(2-methoxyethyl)-6-oxo-1, 6-dihydro-pyridine-2-carboxylic acid

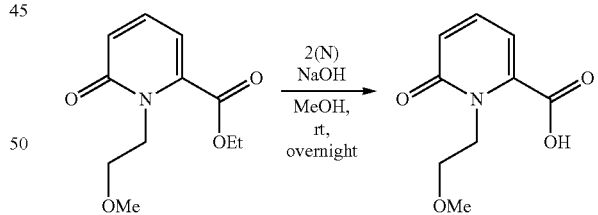

65 mg (0.288 mmol) of 1-(2-methoxyethyl)-6-oxo-1,6-dihydro-pyridine-2-carboxylic acid ethyl ester obtained in Step 1 was dissolved in 2 mL of methanol and to it 1 mL aqueous 2(N) NaOH solution was added. The reaction mixture was stirred at room temperature overnight. After the completion of reaction, the reaction mixture was concentrated under reduced pressure and to the residue 2(N) HCl solution was added until the pH of the reaction mixture became 2. The resulting mixture was extracted with 10% methanol in dichloromethane. The collected organic layer was dried over anhydrous $Na_2SO_4$ and concentrated under vacuum to yield 53 mg of title compound. LC-MS: 198.3 (M+H)

Step 3: 1-(2-Methoxyethyl)-6-oxo-1,6-dihydro-pyridine-2-carboxylic acid N'-(4-fluorophenyl)-hydrazide

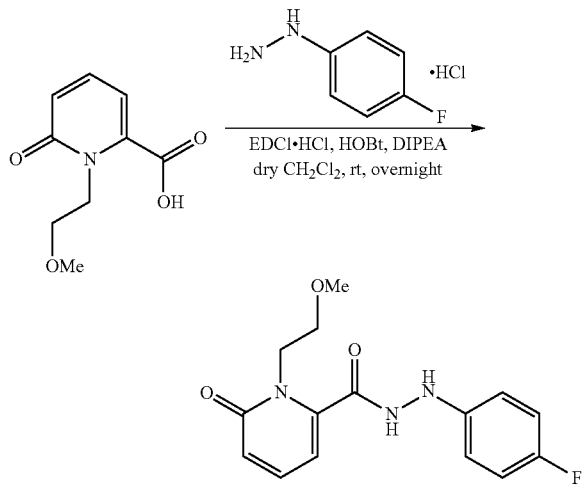

52 mg (0.263 mmol, 1 equiv.) of 1-(2-methoxyethyl)-6-oxo-1,6-dihydropyridine-2-carboxylic acid obtained in Step 3 were dissolved in 5 mL of dry dichloromethane and to it DIPEA (3 equiv.), EDCI.HCl (1.3 equiv) and HOBt (1 equiv.) were added. After 10 min stirring at 0° C., (4-fluorophenyl)-hydrazine hydrochloride (1.5 equiv.) was added. The reaction mixture was allowed to stir overnight at room temperature under nitrogen atmosphere. After the completion of the reaction, solvent was removed and the residue was washed with brine (two times, 5 mL) and extracted with dichloromethane (three times, 10 mL). The collected organic phase was dried over anhydrous $Na_2SO_4$, and concentrated under reduced pressure. The crude product was purified by column chromatography to obtain 22.8 mg of pure title compound (19%).

$^1$H NMR (500 MHz, $CDCl_3$) δ: 3.42 (s, 3H), 3.78-3.80 (m, 2H), 4.37-4.39 (m, 2H), 6.44-6.46 (m, 1H), 6.68-6.70 (m, 1H), 6.89-6.92 (m, 2H), 6.97-7.05 (m, 2H), 7.35-7.38 (m, 1H), 8.76 (s, 1H); LC-MS: 306.5 (M+H); Purity (HPLC): 97.97%.

Example 4

1-Difluoromethyl-6-oxo-1,6-dihydro-pyridine-2-carboxylic acid N'-(4-fluorophenyl)-hydrazide Title compound was prepared by coupling 1-difluoromethyl-6-oxo-1,6-dihydro-pyridine-2-carboxylic acid with (4-fluorophenyl)-hydrazine hydrochloride, using EDCI.HCl, $Et_3N$ and DMAP, according to an analogous method as described in Step 4 of Example 2, using the same solvents, reaction and purification conditions, to obtain title compound (25%). LC-MS: 296.3 (M−H); Purity (HPLC): 96.6%.

Example 5

1-Benzyl-6-oxo-1,6-dihydro-pyridine-2-carboxylic acid N'-(4-fluorophenyl)-hydrazide Title compound was prepared by coupling 1-benzyl-6-oxo-1,6-dihydro-pyridine-2-carboxylic acid with (4-fluorophenyl)-hydrazine hydrochloride, using HATU and DIPEA, according to an analogous method as described in Example 1, using the same solvents, reaction and purification conditions, to obtain title compound (15%). LC-MS: 338.0 (M+H); Purity (HPLC): 95.3%.

Example 6

1-Cyclopropylmethyl-6-oxo-1,6-dihydro-pyridine-2-carboxylic acid N'-(4-fluorophenyl)-hydrazide Title compound was prepared by coupling 1-cyclopropyl-6-oxo-1,6-dihydro-pyridine-2-carboxylic acid with (4-fluorophenyl)-hydrazine hydrochloride, using HATU and DIPEA, according to an analogous method as described in Example 1, using the same solvents, reaction and purification conditions, to obtain title compound (19%). LC-MS: 303.1 (M+H); Purity (HPLC): 96.6%.

Example 7

1-(Prop-2-yn-1-yl)-6-oxo-1,6-dihydropyridine-2-carboxylic acid N'-(4-fluorophenyl)-hydrazide

Step 1: Methyl 6-oxo-1,6-dihydropyridine-2-carboxylate

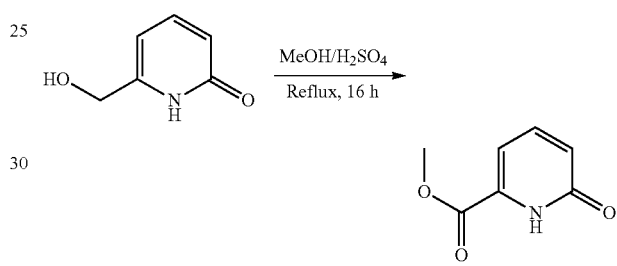

Concentrated sulfuric acid (0.9 mL) was slowly added to a stirred solution of 6-hydroxypicolinic acid (1 g, 7.194 mmol) in methanol (15 mL), and the reaction mixture was refluxed under nitrogen atmosphere for 10 h. Excess of methanol was evaporated under reduced pressure and 10% aqueous $NaHCO_3$ solution was added slowly until pH 7-8. The resultant mixture was extracted with ethyl acetate (2×25 mL) and 5% methanol in dichloromethane (2×25 mL). The combined organic layer was dried over $Na_2SO_4$, filtered and concentrated to give 800 mg (72% yield) of the title compound as white solid.

$^1$H NMR (400 MHz, $CDCl_3$) δ: 7.47 (1H, dd, J=9.04 Hz, 6.88 Hz), 6.98 (1H d, J=6.68 Hz), 6.83 (1H, d, J=9.2 Hz), 3.97 (3H, s).

Step 2: Methyl 6-oxo-1-(prop-2-yn-1-yl)-1,6-dihydropyridine-2-carboxylate

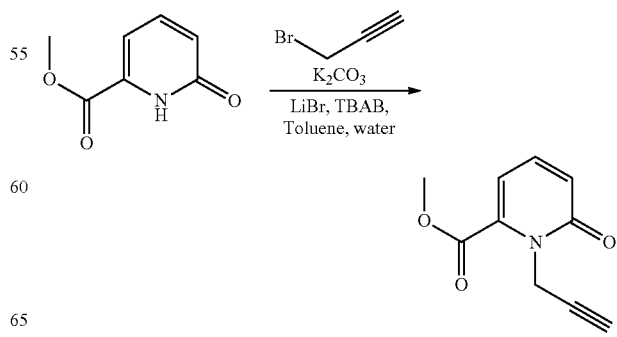

Potassium carbonate (900 mg, 6.511 mmol), lithium bromide (560 mg, 6.511 mmol), tetrabutylammonium bromide (0.1 mg, 0.310 mmol) and propargyl bromide (580 mg, 4.901 mmol) were added to a stirred solution of methyl 6-oxo-1,6-dihydropyridine-2-carboxylate (500 mg, 3.267 mmol) in a mixture of water (0.2 mL) and toluene (8.3 mL). The reaction mixture was stirred at 80° C. for 20 min. The inorganic residue was removed by filtration over a pad of celite and washed with $CH_2Cl_2$. The filtrate was concentrated under reduced pressure. The residue was purified by column chromatography (silica gel 100-200 mesh) to afford 150 mg (24% yield) of the title compound as pale yellow solid.

$^1$H NMR (400 MHz, $CDCl_3$) δ: 7.33-7.29 (1H, m), 6.82 (1H d, J=5.84 Hz), 6.74 (1H, d, J=7.96 Hz), 5.21 (2H, d, J=1.44 Hz), 3.95 (3H, s).

Step 3: 6-Oxo-1-(prop-2-yn-1-yl)-1,6-dihydropyridine-2-carboxilic acid

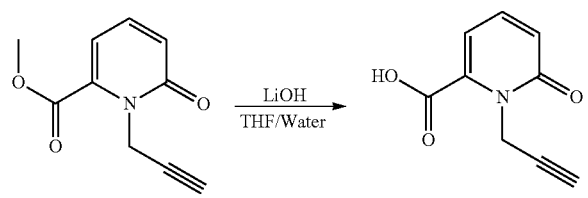

Lithium hydroxide monohydrate (60 mg, 1.428 mmol) was added at 0° C. to a stirred solution of methyl 6-oxo-1-(prop-2-yn-1-yl)-1,6-dihydropyridine-2-carboxylate(150 mg, 0.784 mmol) in THF (1.95 mL) and water (0.6 mL). After being stirred for 10 min. at the same temperature, the solvent was removed under reduced pressure and the residue was re-dissolved in water. The pH of the solution was adjusted to 4-5 using 1N HCl. The resultant solid was filtered and dried to get 100 mg (76% yield) of the title compound as an off-white solid.

$^1$H NMR (400 MHz, DMSO-d6) δ: 14.16 (1H, bs), 7.48 (1H, t, J=8.72 Hz), 6.82 (1H d, J=6.56 Hz), 6.64 (1H, d, J=9.2 Hz), 5.05 (2H, s), 3.2 (1H, s).

Step 4: 1-(Prop-2-yn-1-yl)-6-oxo-1,6-dihydropyridine-2-carboxylic acid N'-(4-fluorophenyl)-hydrazide

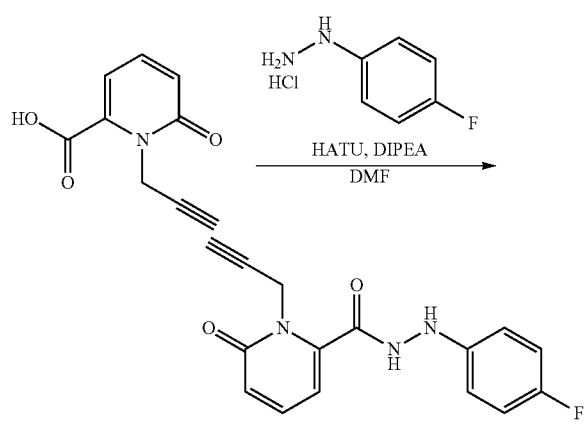

DIPEA (0.3 mL, 1.693 mmol), 4-fluorophenylhydrazine hydrochloride (120 mg, 0.615 mmol) and HATU (320 mg, 0.842 mmol) were added at 0° C. under nitrogen to a stirred solution of 6-oxo-1-(prop-2-yn-1-yl)-1,6-dihydropyridine-2-carboxilic acid (100 mg, 0.564 mmol) in DMF (1.5 mL). The reaction mixture was stirred at room temperature for 1 h, quenched with ice-water (5 mL) and extracted with ethyl acetate (2×20 mL). The combined organic layer was washed with water (1×10 mL), brine (10 mL), dried over anhydrous $Na_2SO_4$ and concentrated under reduced pressure. The crude compound was purified by preparative TLC to afford 30 mg of the title compound as pale yellow solid.

$^1$H NMR (400 MHz, DMSO-d6) δ: 10.73 (1H, d, J=2.88 Hz), 8.03 (1H, d, J=2.88 Hz), 7.52 (1H, dd, J=9.24 Hz, 6.76 Hz), 7.0 (2H, t, J=8.84 Hz), 6.89-6.81 (2H, m), 6.62-6.57 (2H, m), 4.91 (2H, d, J=2.28 Hz), 3.3 (1H, s); LC-MS, m/z, [m−H]: 284.

Example 8

6-Oxo-1-(2,2,2-trifluoroethyl)-1,6-dihydropyridine-2-carboxylic acid N'-(4-fluorophenyl)-hydrazide Step 1: Methyl 6-oxo-1, 6-dihydropyridine-2-carboxylate This compound was prepared as described in step 1 of Example 7.

Step 2: Methyl 6-oxo-1-(2, 2, 2-trifluoromethyl)-1, 6-dihydropyridine-2-carboxylate

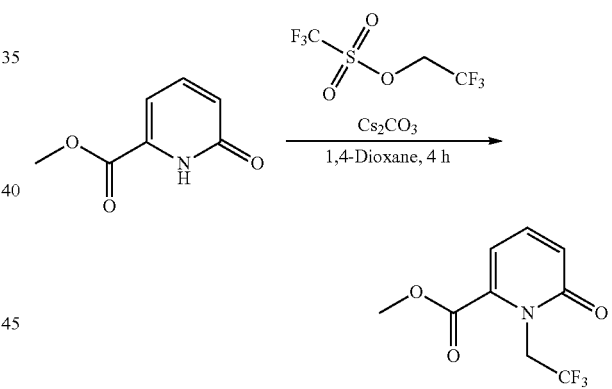

2,2,2-Trifluoroethyl trifluoromethanesulfonate (1.8 g, 7.843 mmol) was added to a stirred suspension of methyl 6-oxo-1,6-dihydropyridine-2-carboxylate (600 mg, 3.92 mmol) and cesium carbonate (2.54 g, 7.843 mmol) in 1,4-dioxane, and the reaction mixture was stirred at 70° C. for 4 h. The inorganic solids were filtered and the solvent was evaporated. The residue was dissolved in ethyl acetate (30 mL), washed with water (20 mL), the organic layer was dried over anhydrous $Na_2SO_4$ and evaporated under reduced pressure to obtain crude compound. The crude compound was purified by column chromatography (silica gel, 100-200 mesh) to afford 280 mg (30% yield) of the title compound as an off-white solid. The structure of the product was further confirmed by NOE experiment (data not shown).

$^1$H NMR (400 MHz, $CDCl_3$) δ: 7.35 (1H, q, J=6.88 Hz), 6.88 (1H, dd, J=1.28 Hz, 6.8 Hz), 6.78 (1H, dd, J=1.24 Hz, J=9.32 Hz), 5.4 (2H, q, J=8.62 Hz,), 3.91 (3H, s).

Step 3: 6-oxo-1-(2,2, 2-trifluoroethyl)-1, 6-dihydropyridine-2-carboxilic acid

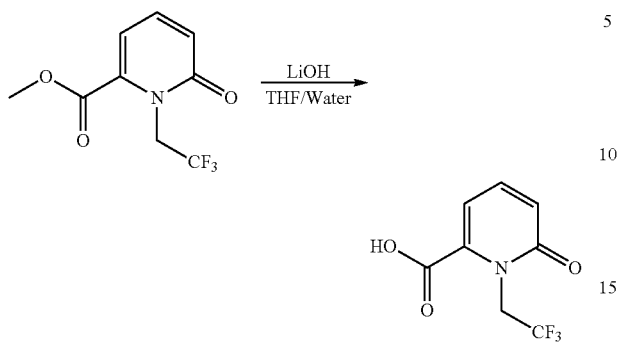

Lithium hydroxide monohydrate (110 mg, 1.428 mmol) was added at 0° C. to a stirred solution of methyl 6-oxo-1-(2,2,2-trifluoromethyl)-1,6-dihydropyridine-2-carboxylate (310 mg, 1.319 mmol) in THF (12 mL) and water (4 mL). The reaction mixture was stirred at room temperature for 30 min. After completion of reaction, THF was evaporated, the residue was diluted with water (5 mL) and the pH was adjusted to 4-5 using 1N HCl. The aqueous layer was extracted with ethyl acetate (2×25 mL). The combined organic layer was washed with water (1×10 mL), brine (10 mL), dried over anhydrous $Na_2SO_4$ and the solvent was evaporated under reduced pressure to afford 250 mg (85% yield) of the title compound as an off-white solid.

$^1$H NMR (400 MHz, DMSO-d6) δ: 14.1 (1H, bs), δ 7.5 (1H, q, J=7 Hz), δ 6.9 (1H, d, J=6.72 Hz), δ 6.7 (1H, d, J=9.2 Hz), δ 5.4 (2H, q, J=9.28 Hz).

Step 4: 6-Oxo-1-(2,2,2-trifluoroethyl)-1,6-dihydropyridine-2-carboxylic acid N'-(4-fluorophenyl)-hydrazide

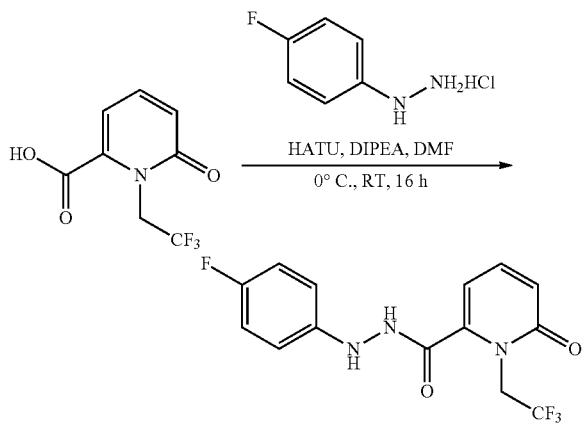

DIPEA (0.22 mL, 1.35 mmol) and HATU (258 mg, 0.678 mmol) were added at 0° C. under nitrogen to a stirred solution of 6-oxo-1-(2,2,2-trifluoroethyl)-1,6-dihydropyridine-2-carboxilic acid (100 mg, 0.452 mmol) in DMF (5 mL). Then the reaction mixture was stirred for 10 minutes at same temperature, and 4-fluorophenylhydrazine hydrochloride (81 mg, 0.497 mmol) was added. The reaction mixture was stirred at room temperature for 16 h, quenched with ice-water (5 mL) and extracted with ethyl acetate (2×15 mL). The combined organic layers were washed with water (1×10 mL), brine solution (10 mL), dried over anhydrous $Na_2SO_4$ and evaporated under reduced pressure. The crude compound was purified by column chromatography (silica gel, 100-200 mesh) to afford 40 mg (27% yield) of the title compound as a pale yellow solid.

$^1$H NMR (400 MHz, DMSO-d6) δ: 10.8 (1H, d, J=2.72 Hz), 8.04 (1H, d, J=2.76 Hz), 7.6 (1H, q, J=6.8 Hz), 7.0 (2H, t, J=8.8 Hz), 6.84 (2H, q, J=2.04 Hz),6.74 (2H, dd, J=18.68 Hz, J=16.72 Hz), 5.16 (2H, q, J=9.35 Hz); LC-MS m/z (M−H): 328.

Example 9

1-Methyl-6-oxo-1,6-dihydropyridine-2-carboxylic acid N'-(4-methoxyphenyl)-hydrazide

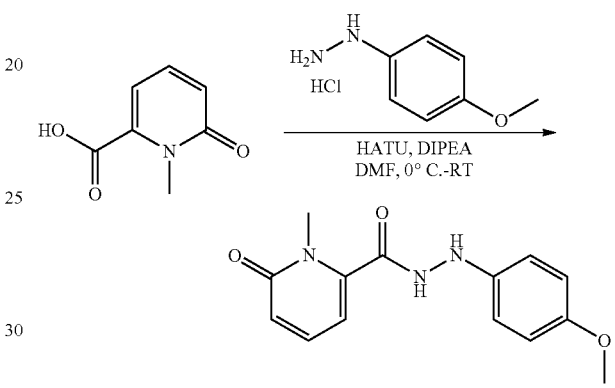

DIPEA (0.68 mL, 3.927 mmol), 4-methoxyphenylhydrazine hydrochloride (250 mg, 1.43 mmol) and HATU (740 mg, 1.947 mmol) were added at 0° C. under nitrogen to a stirred solution of 1-methyl-6-oxo-1,6-dihydropyridine-2-carboxilic acid (200 mg, 1.30 mmol) in DMF (3 mL). The reaction mixture was stirred at room temperature for 1 h, quenched with ice-water (5 mL), and extracted with ethyl acetate (2×25 mL). The combined organic layer was washed with water (1×10 mL), brine (10 mL), dried over anhydrous $Na_2SO_4$ and concentrated under reduced pressure. The crude compound was triturated with $CH_2Cl_2$ and EtOAc, a solid was formed and was filtered and dried to get 30 mg (8% yield) of the title compound as an off-white solid.

$^1$H NMR (400 MHz, DMSO-d6): δ 10.55 (1H, d, J=2.88 Hz), 7.74 (1H, d, J=3.0 Hz), 7.48 (1H, dd, J=9.16, 6.76 Hz), 6.81-6.76 (4H, m), 6.52 (1H, dd, J=9.12, 0.96 Hz), 6.44 (1H, dd, J=6.64, 1.04 Hz), 3.7 (3H, s), 3.38 (3H, s); LC-MS: m/z, [m+H]: 274.

Example 10

1-Methyl-6-oxo-1,6-dihydropyridine-2-carboxylic acid N'-(4-chlorophenyl)-hydrazide

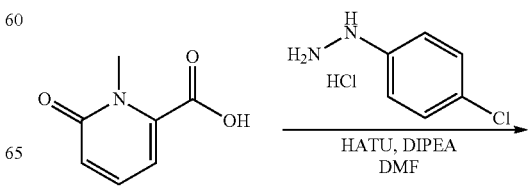

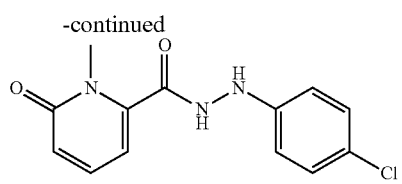

DIPEA (505 mg, 3.90 mmol), 4-chlorophenyl hydrazine HCl (258 mg, 1.42 mmol) and HATU (744 mg, 1.98 mmol) were added at 0° C. under nitrogen atmosphere to a stirred solution of 1-methyl-6-oxo-1,6-dihydropyridine-2-carboxylic acid (200 mg, 1.307 mmol) in DMF (2 mL). The reaction mixture was stirred at room temperature for 2 h, quenched with ice-water (15 mL), and extracted with ethyl acetate (2×10 mL). The combined organic layer was washed with water (1×10 mL), brine (10 mL), dried over anhydrous $Na_2SO_4$ and concentrated under reduced pressure. The crude compound was purified by column chromatography (silica gel, 100-200 mesh) to give 100 mg (27% yield) of the title compound as an off-white solid.

$^1$H NMR (400 MHz, DMSO-d6) δ: 10.62 (s, 1H), δ 8.24 (s, 1H), δ 7.50-7.46 (m, 1H), δ 7.20 (d, J=8.52 Hz, 2H), δ 6.81 (d, J=8.6 Hz, 2H), δ 6.55-6.47 (m, 2H), δ 3.38 (s, 3H); LC-MS m/z (M+H): 278.16.

Example 11

1-Methyl-6-oxo-1,6-dihydropyridine-2-carboxylic acid N'-(4-methylphenyl)-hydrazide

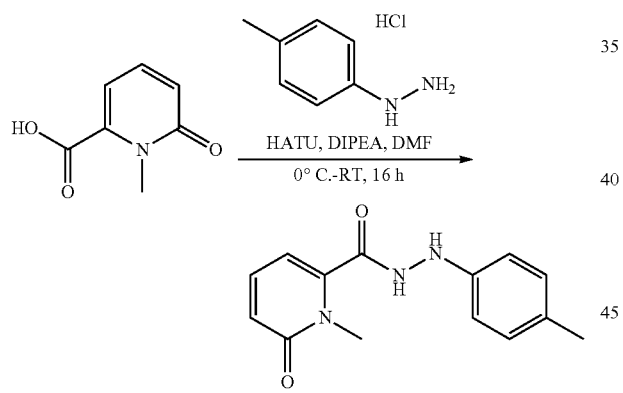

DIPEA (0.85 mL, 4.891 mmol), 1-methyl-6-oxo-1,6-dihydropyridine-2-carboxylic acid (250 mg, 1.633 mmol) and HATU (930 mg, 2.447 mmol) were added at 0° C. under nitrogen to a stirred solution of 4-methylphenylhydrazine HCl (284 mg, 1.790 mmol) in DMF (5 mL). The reaction mixture was stirred at room temperature for 16 h, quenched with ice-cold water (5 mL), and extracted with ethyl acetate (3×10 mL). The combined organic layer was washed with water (1×10 mL), brine (10 mL), dried over anhydrous $Na_2SO_4$ and evaporated under reduced pressure. The crude compound was purified by column chromatography (silica gel, 100-200 mesh) to afford 26 mg (6% yield) of the title compound as an off-white solid.

$^1$H NMR (400 MHz, DMSO-d6) δ: 10.54 (bs, 1H), 7.88 (bs, 1H), δ 7.47 (t, 1H, J=7.16 Hz), δ 6.99 (d, 2H, J=7.72 Hz), 6.72 (d, 2H, J=7.92 Hz), 6.52 (d, 1H, J=9 Hz), 6.45 (d, 1H, J=6.36 Hz), 3.38 (s, 3H), 2.18 (s, 3H); LC-MS m/z (M+H): 258.2.

Example 12

1-Methyl-6-oxo-1,6-dihydropyridine-2-carboxylic acid N'-(2,4-difluorophenyl)-hydrazide

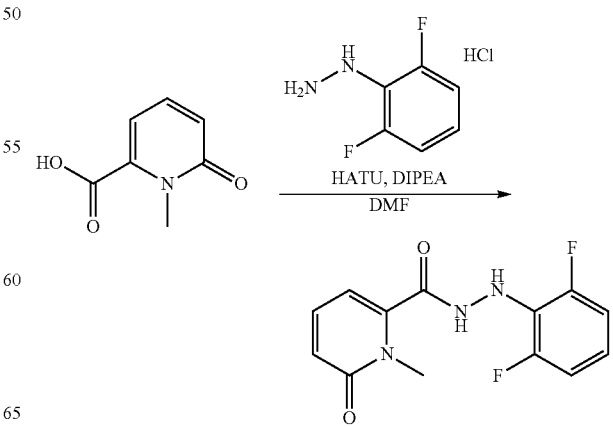

DIPEA (0.52 mL, 2.938 mmol), (2,4-difluorophenyl)hydrazine hydrochloride (194 mg, 1.077 mmol) and HATU (558.3 mg, 1.469 mmol) were added at 0° C. under nitrogen to a stirred solution of 1-methyl-6-oxo-1,6-dihydropyridine-2-carboxylic acid (150 mg, 0.979 mmol) in DMF (1.5 mL). The reaction mixture was stirred at room temperature for 1 h, quenched with ice-cold water (5 mL), and extracted with ethyl acetate (2×10 mL). The combined organic layer was washed with water (1×10 mL), brine (10 mL), dried over anhydrous $Na_2SO_4$ and concentrated under reduced pressure. The crude compound was purified by column chromatography (silica gel, 60-120 mesh) to afford 35 mg (12% yield) of the title compound as an off-white solid.

$^1$H NMR (400 MHz, DMSO-d6) δ: 10.62 (bs, 1H), 7.92 (bs, 1H), δ 7.49-7.46 (dd, 1H, J=6.76 Hz, J=9.16 Hz), δ 7.2-7.15 (m, 2H), 6.92 (t, 1H, J=5.3 Hz), 6.55-6.45 (m, 2H), 3.4 (s, 3H); LC-MS m/z (M−H): 278.

Example 13

1-Methyl-6-oxo-1,6-dihydropyridine-2-carboxylic acid N'-(2,6-difluorophenyl)-hydrazide DIPEA (0.85 mL, 4.891 mmol), 1-methyl-6-oxo-1,6-dihydropyridine-2-carboxylic acid (250 mg, 1.633 mmol) and HATU (930 mg, 2.447 mmol) were added at 0° C. under nitrogen to a stirred solution of 2,6-difluorophenylhydrazine HCl (324 mg, 1.794 mmol) in DMF (5 mL). The reaction mixture was stirred at room temperature for 16 h, quenched with ice-cold water (5 mL), and extracted with ethyl acetate (2×10 mL). The combined organic layer was washed with water (1×10 mL), brine (10 mL), dried over anhydrous Na$_2$SO$_4$ and evaporated under reduced pressure. The crude compound was purified by column chromatography (silica gel, 100-200 mesh) to afford 31 mg (~7% yield) of the title compound as an off-white solid.

$^1$H NMR (400 MHz, DMSO-d6) δ: 10.8 (bs, 1H), 7.81 (s, 1H), δ 7.45 (s, 1H), δ 7.00 (s, 2H), 6.87 (s, 1H), 6.52 (d, J=7.8 Hz, 1H), 6.25 (s, 1H), 3.33 (d, 3H); LC-MS m/z (M+H): 280.

Example 14

1-(2-(Dimethylamino)-2-oxoethyl)-6-oxo-1,6-dihydropyridine-2-carboxylic acid N'-(4-fluorophenyl)-hydrazide Step 1: Methyl 1-(2-(dimethylamino)-2-oxoethyl)-6-oxo-1,6-dihydropyridine-2-carboxylate

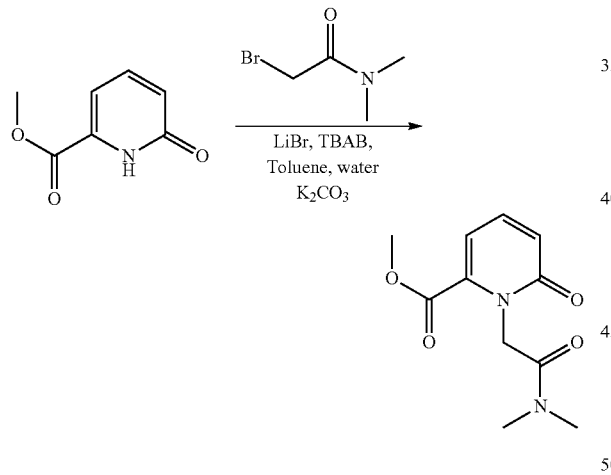

Water (0.2 mL), potassium carbonate (1.26 g, 9.09 mmol), lithium bromide (794 mg, 9.14 mmol), tetrabutylammonium bromide (147.40 mg, 0.457 mmol) and N,N-dimethyl bromoacetamide (1.06 g, 6.38 mmol) were added to a stirred solution of methyl 6-oxo-1,6-dihydropyridine-2-carboxylate (700 mg, 4.57 mmol) in toluene (23 mL). The reaction mixture was stirred at reflux temperature for 1 h. The progress of reaction was monitored by TLC. The reaction mixture was filtered through a pad of celite and washed with ethyl acetate (10 mL), the filtrate was concentrated under reduced pressure to afford crude compound, which was purified by column chromatography (silica gel, 100-200 mesh), to obtain 600 mg (55% yield) of the title compound as an off-white solid.

$^1$H NMR (400 MHz, CDCl$_3$) δ: 7.7 (2H, t, 4.04 Hz), δ 7.1 (1H, t, J=4.56 Hz), δ 5.1 (2H, s), δ 3.9 (3H, s), δ 3.1 (3H, s), δ 3.0 (3H, s).

Step 2: 1-(2-(Dimethylamino)-2-oxoethyl)-6-oxo-1,6-dihydropyridine-2-carboxylic acid

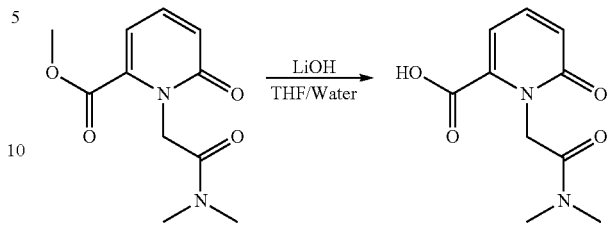

Lithium hydroxide (211 mg, 5.02 mmol) was added at 0° C. to a stirred solution of methyl 1-(2-di methylamino-2-oxoethyl)-6-oxo-1,6-dihydropyridine-2-carboxylate (600 mg, 2.52 mmol) in THF and water (6 mL, 3:1), and stirred at same temperature for 15 min. After completion of reaction, the reaction mixture was concentrated, diluted with water (10 mL). The pH of the solution was adjusted to 3 using aqueous HCl, the aqueous layer was extracted with ethyl acetate (3×25 mL), dried over anhydrous sodium sulfate and concentrated under reduced pressure to get 375 mg (66% yield) of the title compound as a white solid.

$^1$H NMR (400 MHz, DMSO-d6) δ: 12.9 (1H, brs), δ 7.9 (1H, m), δ 7.65 (1H, t, J=7.24 Hz), δ 7.1 (1H, t, J=8.16 Hz), δ 5.1 (2H, s), δ 3.0 (3H, s), δ 2.8 (3H, s).

Step 3: 1-(2-(Dimethylamino)-2-oxoethyl)-6-oxo-1,6-dihydropyridine-2-carboxylic acid N'-(4-fluorophenyl)-hydrazide

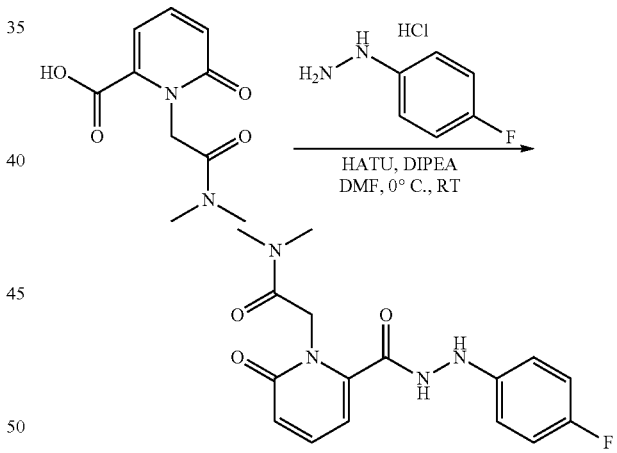

DIPEA (0.460 mL, 2.63 mmol), HATU (509 mg, 1.33 mmol) and 4-fluorophenylhydrazine hydrochloride (159.6 mg, 0.97 mmol) was added at 0° C. under nitrogen to a stirred solution of 1-(2-dimethylamino-2-oxoethyl)-6-oxo-1,6-dihydropyridine-2-carboxylic acid (200 mg, 0.84 mmol) in DMF (3 mL). The reaction mixture was stirred at room temperature for 45 minutes, quenched with ice-water (10 mL), and extracted with ethyl acetate (3×20 mL). The combined organic layer was washed with water (1×10 mL), brine (10 mL), dried over anhydrous Na$_2$SO$_4$ and concentrated. The crude compound was purified by column chromatography (silica gel, 100-200 mesh) to obtain 35 mg (11% yield) of the title compound as an off-white solid.

$^1$H NMR (400 MHz, DMSO-d6) δ: 10.3 (1H, s), 7.94 (1H, d, J=3 Hz), 7.88 (1H, t, J=7.92 Hz), 7.6 (1H, d, J=7.24 Hz), 7.1 (1H, d, J=8.32 Hz), 7.0 (2H, t, J=8.8 Hz), 6.75 (2H, m), 5.3 (2H, s), 3.0 (3H, s), 2.85 (3H, s); LC-MS m/z [m+H] 333.

Example 15

1-(2-Amino-2-oxoethyl)-6-oxo-1,6-dihydropyridine-2-carboxylic acid N'-(4-fluorophenyl)-hydrazide Step 1: Methyl 1-(2-amino-2-oxoethyl)-6-oxo-1, 6-dihydropyridine-2-carboxylate

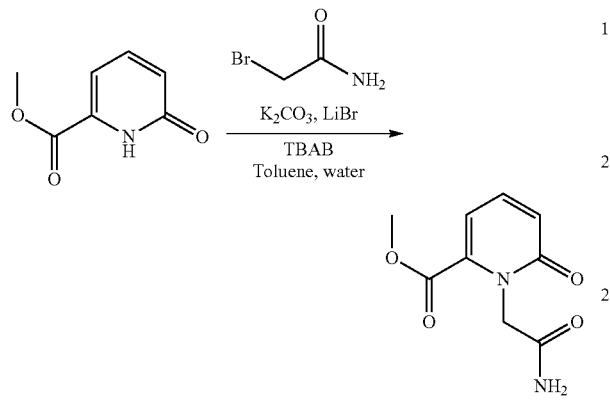

Water (0.2 mL), potassium carbonate (1.35 g, 9.74 mmol), lithium bromide (850 mg, 9.79 mmol), tetrabutylammonium bromide (157.80 mg, 0.489 mmol) and 2-bromoacetamide (1.01 g, 7.34 mmol) was added to a stirred solution of methyl 6-oxo-1,6-dihydropyridine-2-carboxylate (750 mg, 4.90 mmol) in toluene (23.5 mL). The reaction mixture was stirred at reflux temperature for 6 h. After completion of reaction, the reaction mixture was filtered through a pad of celite, washed with ethyl acetate, the filtrate was concentrated under reduced pressure to afford crude compound, which was purified by column chromatography (silica gel, 100-200 mesh) to obtain 180 mg (17% yield) of the title compound as white solid.

$^1$H NMR (400 MHz, DMSO-d6) δ: 7.9 (1H, t, J=7.4 Hz), 7.7 (1H, d, J=6.76 Hz), 7.5 (1H, s), 7.2 (1H, s), 7.15 (1H, d, J=7.76 Hz), 4.7 (2H, s), 3.8 (3H, s).

Step 2: 1-(2-Amino-2-oxoethyl)-6-oxo-1, 6-dihydropyridine-2-carboxylic acid

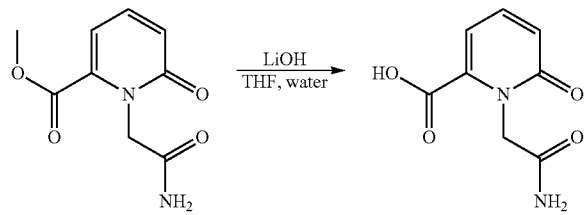

Lithium hydroxide (72 mg 1.74 mmol) was added at 0° C. to a stirred solution of methyl 1-(2-amino-2-oxoethyl)-6-oxo-1,6-dihydropyridine-2-carboxylate (180 mg, 0.856 mmol) in THF and water (1.8 mL, 3:1), and the mixture was stirred for 15 min at same temperature. After completion of the reaction, the reaction mixture was concentrated, diluted with water (5 mL), acidified with diluted HCl (pH=3), the solid formed was filtered and dried to afford 75 mg (44% yield) of the title compound as a white solid.

$^1$H NMR (400 MHz, DMSO-d6) δ: 13 (1H s), 7.9 (1H, t, J=7.96 Hz), 7.65 (1H d, J=7.28 Hz), 7.5 (1H, s), 7.2 (1H, s), 7.1 (1H, d, J=7.72 Hz), 4.9 (1H, s), 4.7 (1H, s).

Step 3: 1-(2-Amino-2-oxoethyl)-6-oxo-1,6-dihydropyridine-2-carboxylic acid N'-(4-fluorophenyl)-hydrazide

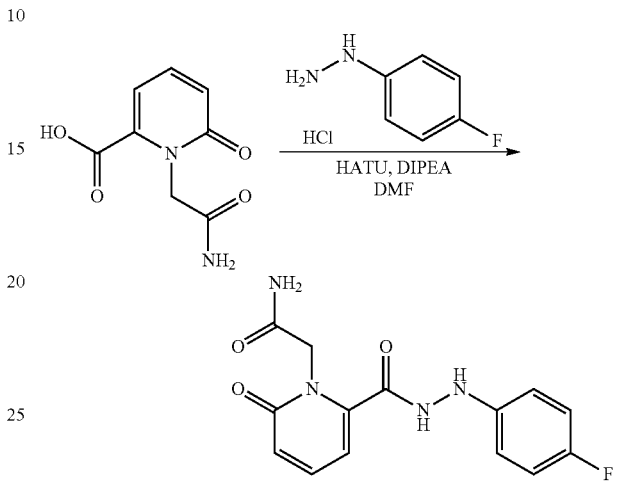

DIPEA (414 mg, 3.20 mmol), HATU (620 mg, 1.63 mmol) and 4-fluoro phenylhydrazine hydrochloride were added at 0° C. under nitrogen to a stirred solution of 1-(2-amino-2-oxoethyl)-6-oxo-1,6-dihydropyridine-2-carboxylic acid (210 mg, 1.071 mmol) in DMF (3 mL). The reaction mixture was stirred at room temperature for 30 min. After completion of the reaction, the reaction mixture was quenched with ice-cold water (10 mL) and extracted with ethyl acetate (2×20 mL). The combined organic layer was washed with water (1×10 mL), brine (10 mL), dried over anhydrous Na$_2$SO$_4$ and concentrated. The crude compound was purified by column chromatography (silica gel, 100-200 mesh) to obtain 35 mg (10% yield) of the title compound as an off-white solid.

$^1$H NMR (400 MHz, DMSO-d6) δ: 10.3 (1H, s), 7.9 (2H, d, J=8.16 Hz), 7.6 (1H, d, J=7.24), 7.5 (1H, s), 7.3 (1H, s) 7.1 (1H, d, J=8.28 Hz), 6.9 (2H, t, J=8.84 Hz), 6.75 (2H, m), 4.9 (2H, s); LC-MS m/z (M+H): 305.13.

Example 16

1-Ethyl-2-oxo-1,2-dihydropyridine-3-carboxylic acid N'-(4-fluorophenyl)-hydrazide Step 1: 1-Ethyl-2-oxo-1, 2-dihydropyridine-3-carboxylic acid

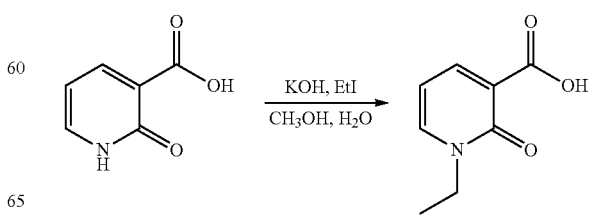

A solution of KOH (1.6 g, 28.76 mmol) in water (3 mL) was added at room temperature to a stirred solution of 2-hydroxynicotinic acid (2 g, 14.38 mmol) in methanol (20 mL). After stirring the reaction mixture for 10 min., ethyl iodide (1.2 mL, 15.82 mmol) was added and stirring was continued at 70° C. for 20 h. Excess of methanol was evaporated under reduced pressure and pH of the solution was adjusted to 2-3 using 1N HCl. The resulting solution was extracted with ethyl acetate (3×50 mL), the combined organic layer was dried over Na$_2$SO$_4$, filtered, the solvent was evaporated under reduced pressure and the crude compound was purified by column chromatography (silica gel 100-200 mesh) to give 0.8 g (34% yield) of the title compound as an off-white solid.

$^1$H NMR (400 MHz, DMSO-d6) δ: 14.67 (s, 1H), 8.36 (dd, J=7.1 Hz, 1.5 Hz, 1H), 8.27 (dd, J=6.4 Hz, 1.5 Hz, 1H), 6.72 (t, J=6.9 Hz, 1H), 4.11 (q, J=7.1 Hz, 2H), 1.29 (t, J=7.1 Hz, 3H).

Step 2: 1-Ethyl-2-oxo-1,2-dihydropyridine-3-carboxylic acid N'-(4-fluorophenyl)-hydrazide

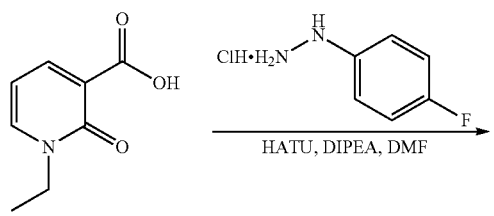

DIPEA (0.3 mL, 1.79 mmol), 4-fluorophenylhydrazine hydrochloride (107 mg, 0.65 mmol) and HATU (341 mg, 0.88 mmol) were added at 0° C. under nitrogen to a stirred solution of 1-ethyl-2-oxo-1,2-dihydropyridine-3-carboxylic acid (100 mg, 0.59 mmol) in DMF (2 mL). The reaction mixture was stirred at room temperature for 1 h, quenched with ice-water (10 mL), and extracted with ethyl acetate (2×25 mL). The combined organic layer was washed with water (2×10 mL), brine (10 mL), dried over anhydrous Na$_2$SO$_4$ and concentrated under reduced pressure. The crude compound was purified by preparative TLC to afford 50 mg (31% yield) of the title compound as an off-white solid.

$^1$H NMR (400 MHz, DMSO-d6) δ: 11.05 (d, J=3.3 Hz, 1H), 8.30 (dd, J=7.2 Hz, 2.1 Hz, 1H), 8.11 (dd, J=6.5 Hz, 2.1 Hz, 1H), 7.9 (d, J=3.4 Hz, 1H), 6.98 (t, J=8.8 Hz, 2H), 6.74-6.71 (m, 2H), 6.55 (t, J=6.9 Hz, 1H), 4.18 (q, J=7.1 Hz, 2H), 1.29 (t, J=7.1 Hz, 3H); LC-MS: m/z 276 (M+1).

Example 17

1-Methyl-2-oxo-1,2-dihydropyridine-3-carboxylic acid N'-(4-fluorophenyl)-hydrazide Step 1: 1-Methyl-2-oxo-1,2-dihydropyridine-3-carboxylic acid

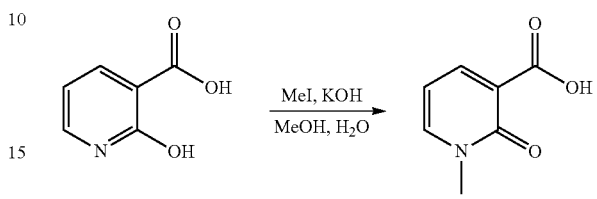

KOH (8 g, 14.37 mmol) and water (0.15 mL, 0.15 Vol), followed by MeI (0.67 mL, 10.78 mmol), were added at 0° C. to a stirred solution of 2-hydroxynicotinic acid (1 g, 7.18 mmol) in MeOH (10 mL, 10 Vol) and the reaction mixture was stirred at 80° C. for 16 h. The reaction mixture was cooled to room temperature, diluted with ice-water (25 mL), and extracted with ethyl acetate (2×25 mL). The combined organic layer was washed with water (25 mL), brine (25 mL), dried over anhydrous Na$_2$SO$_4$ and concentrated under reduced pressure to afford 500 mg (45% yield) of the title compound as an off-white solid.

$^1$H NMR (400 MHz, DMSO-d6) δ: 14.65 (1H, s), 8.36 (1H, dd, J=7.32 Hz, J=2.0 Hz), 8.24 (1H, dd, J=6.52 Hz, J=2.0 Hz), 6.7 (1H, t, J=7.04 Hz), 3.64 (3H, s).

Step 2: 1-Methyl-2-oxo-1,2-dihydropyridine-3-carboxylic acid N'-(4-fluorophenyl)-hydrazide

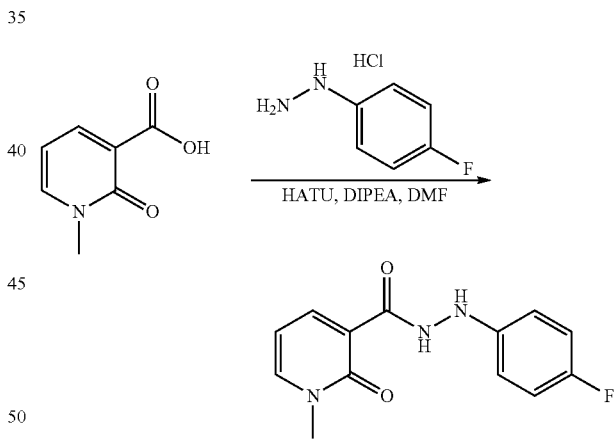

DIPEA (0.74 mL, 5.299 mmol), 4-fluorophenylhydrazine hydrochloride (233 mg, 1.437 mmol) and HATU (745 mg, 1.960 mmol) were added at 0° C. under nitrogen to a stirred solution of 1-methyl-2-oxo-1,2-dihydropyridine-3-carboxylic acid (200 mg, 1.306 mmol) in DMF (3 mL). The reaction mixture was stirred at room temperature for 1 h. The reaction mixture was diluted with ice-water (20 mL), extracted with ethyl acetate (2×50 mL), the combined organic layer was washed with water (1×15 mL), brine (15 mL), dried over anhydrous Na$_2$SO$_4$ and concentrated under reduced pressure. The crude compound was purified by preparative TLC to afford 35 mg (10% yield) of the title compound as an off-white solid.

$^1$H NMR (400 MHz, DMSO-d6) δ: 11.08 (1H, bs), 8.3 (1H, dd, J=7.28 Hz, J=2.16 Hz), 8.1 (1H, dd, J=6.48 Hz,

J=2.12 Hz), 7.98 (1H, bs), 7.0 (2H, m), 6.75 (2H, m), 6.51 (1H, t, J=6.64 Hz), 3.6 (3H, s); LC-MS m/z [m+H]: 262.

Example 18

1-Methyl-2-oxo-1,2-dihydropyridine-4-carboxylic acid N'-(4-fluorophenyl)-hydrazide

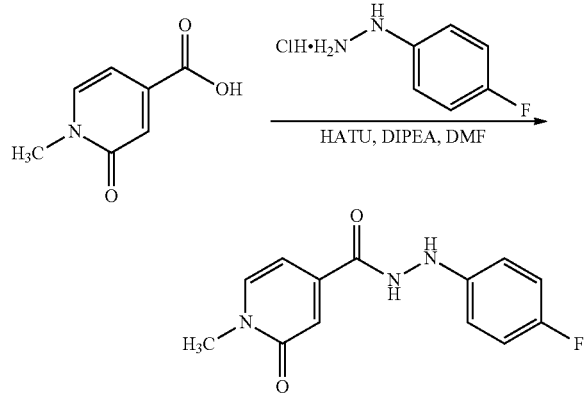

DIPEA (0.35 mL, 1.95 mmol), 4-fluorophenylhydrazine hydrochloride (117 mg, 0.71 mmol) and HATU (372 mg, 0.97 mmol) were added at 0° C. under nitrogen to a stirred solution of 1-methyl-2-oxo-1,2-dihydropyridine-4-carboxylic acid (100 mg, 0.65 mmol) in DMF (2 mL). The reaction mixture was stirred at room temperature for 1 h, quenched with ice-water (10 mL), extracted with ethyl acetate (2×25 mL), the combined organic layer was washed with water (1×10 mL), brine (10 mL), dried over anhydrous $Na_2SO_4$ and concentrated under reduced pressure. The crude compound was purified by preparative TLC to afford 40 mg (24% yield) of the title compound as an off-white solid.

$^1$H NMR (400 MHz, DMSO-d6) δ: 10.46 (bs, 1H), 7.90 (s, 1H), 7.80 (d, J=7.0 Hz, 1H), 6.98 (t, J=8.8 Hz, 2H), 6.87-6.85 (m, 1H), 6.77-6.73 (m, 2H), 6.51 (dd, J=6.9 Hz, 1.8 Hz, 1H), 3.44 (s, 3H); LC-MS: m/z 260 (M-1).

Example 19

1-Methyl-6-oxo-1,6-dihydropyridine-3-carboxylic acid N'-(4-fluorophenyl)-hydrazide

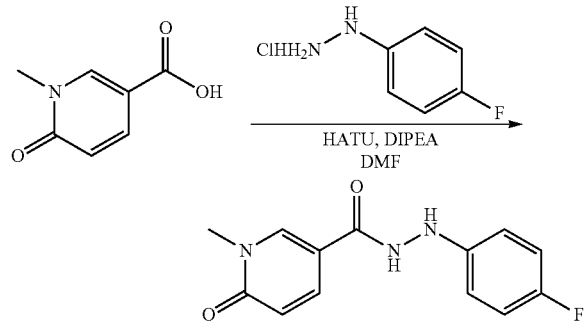

DIPEA (210 mg, 1.63 mmol), 4-fluorophenylhydrazine hydrochloride (132.8 mg, 0.816 mmol) and HATU (310 mg, 0.816 mmol) were added at 0° C. under nitrogen to a stirred solution of 1-methyl-6-oxo-1,6-dihydropyridine-2-carboxylic acid (100 mg, 0.653 mmol) in DMF (2 mL). The reaction mixture was stirred at room temperature for 2 h, quenched with ice-water (10 mL), and extracted with ethyl acetate (2×10 mL). The combined organic layer was washed with water (1×10 mL), brine (10 mL), dried over anhydrous $Na_2SO_4$ and concentrated under reduced pressure. The crude compound was purified by column chromatography (silica gel 100-200 mesh) to afford 50 mg (29% yield) of the title compound as an off-white solid.

$^1$H NMR (400 MHz, DMSO-d6) δ: 10.09 (s, 1H), 8.41 (s, 1H), 7.87 (dd, J=9.4 Hz, 2.4 Hz, 1H), 7.80 (d, J=2.56 Hz 1H), 6.96 (t, J=8.88 Hz, 2H), 6.77-6.74 (m, 2H), 6.42 (d, J=9.48 Hz 1H), 3.48 (s, 3H); LC-MS m/z (M-H): 260.1.

Example 20

1-Methyl-6-oxo-1,6-dihydropyridine-2-carboxylic acid N'-(4-fluorophenyl)-N'-methyl-hydrazide

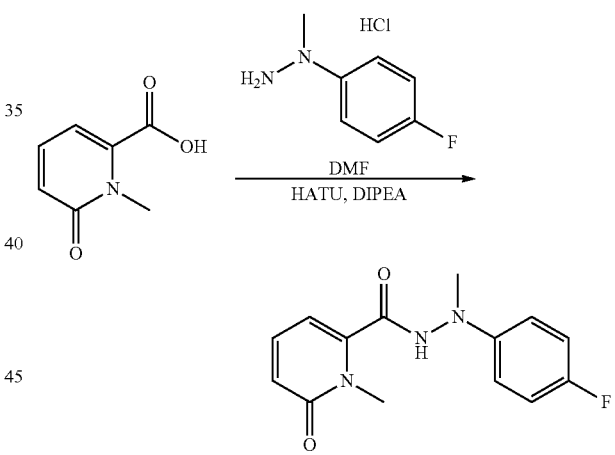

DIPEA (0.85 mL, 4.87 mmol) followed by HATU (931 mg, 2.45 mmol) and N-(4-fluorophenyl)-N-methylhydrazine hydrochloride (317 mg, 1.95 mmol) were added at 0° C. under nitrogen to a stirred solution of 1-methyl-6-oxo-1,6-dihydropyridine-2-carboxylic acid (250 mg, 1.633 mmol) in DMF (3.75 mL). The reaction mixture was stirred at room temperature for 45 min., quenched with ice-water (15 mL), and extracted with ethylacetate (3×25 mL). The combined organic layer was washed with water (1×20 mL), brine (20 mL), dried over anhydrous $Na_2SO_4$ and concentrated. The crude compound was purified by column chromatography (silica gel, 100-200 mesh), to get 70 mg (15% yield) of the title compound as a beige color solid.

$^1$H NMR (400 MHz, DMSO-d6) δ; 10.85 (1H, s), 7.48 (1H, t, J=8.76 Hz) 7.05 (2H, t, J=8.68 Hz), 6.86 (2H, m), 6.55 (2H, m), 3.4 (3H, s), 3.2 (3H, s).

Example 21

4-Methoxy-1-methyl-6-oxo-1,6-dihydropyridine-2-carboxylic acid N'-(4-fluorophenyl)-hydrazide Step 1: 4-Methoxy-2-(methoxycarbonyl)pyridine 1-oxide

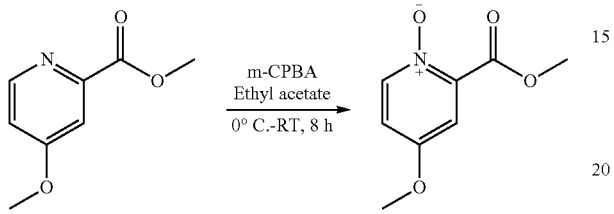

mCPBA (28.37 g, 164.5 mmol) was added at 0° C. to a stirred solution of methyl-4-methoxypicolinate (5.5 g, 32.89 mmol) in ethyl acetate (110 mL). The resulting reaction mixture was stirred at room temperature for 8 h. The reaction mixture was quenched with saturated sodium bicarbonate solution (50 mL) and the ethyl acetate layer was separated. The aqueous layer was extracted with 10% methanol in dichloromethane (5×50 mL). The combined organic layer was dried over anhydrous $Na_2SO_4$, filtered and solvent was evaporated under reduced pressure to afford 3 g (72% yield) of the title compound as an off-white solid.

MS: [M+H]+ 184.

Step 2: Methyl 6-hydroxy-4-methoxypicolinate

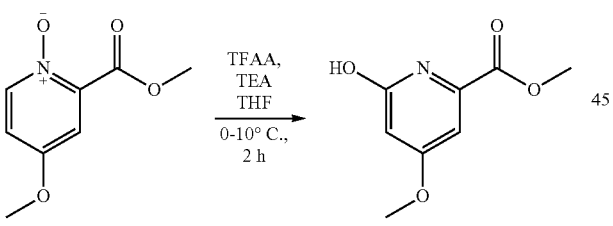

TFAA (5.4 mL, 43.71 mmol) and triethylamine (6 mL, 3 v) were added at 0° C. over a period of 15 min to a solution of 4-methoxy-2-(methoxycarbonyl)pyridine-1-oxide (2 g, 10.92 mmol) in dry THF (60 mL). The resulting reaction mixture was stirred at 0-10° C. for 2 h. The solvent was evaporated under reduced pressure; the residue was dissolved in 100 mL of dichloromethane and washed with water (1×25 mL). The organic layer was dried over anhydrous $Na_2SO_4$ and concentrated under reduced pressure to obtain crude compound. The crude compound was purified by (silica gel 100-200 mesh) column chromatography to afford 1 g (50% yield) of the title compound as an off-white solid.

$^1$H NMR (400 MHz, CDCl$_3$) δ: 11.16 (1H, bs), 6.60 (1H, s), 6.03 (1H, d, J=1.72), 3.82 (3H, s), 3.77 (3H, s).

Step 3: Methyl 4-methoxy-1-methyl-6-oxo-1,6-dihydropyridine-2-carboxylate

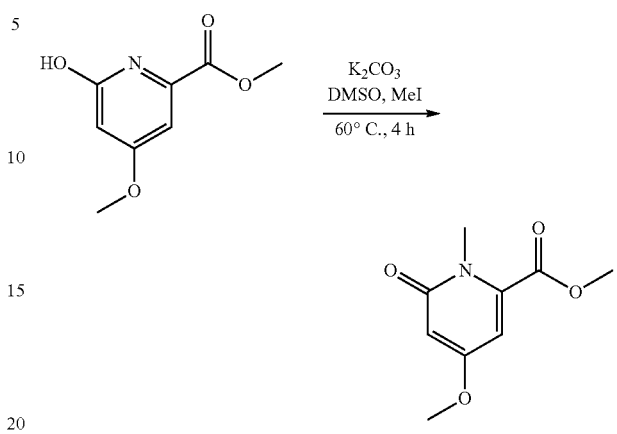

$K_2CO_3$ (750 mg, 5.46 mmol) and methyl iodide (0.5 mL, 8.19 mmol) were added to a stirred solution of methyl 6-hydroxy-4-methoxypicolinate (500 mg, 2.73 mmol) in DMSO (5 mL). The reaction mixture was stirred at 60° C. for 2 h, cooled to room temperature, diluted with water (30 mL) and extracted with ethyl acetate (2×25 mL). The combined organic layer was washed with water (1×10 mL), brine solution (10 mL) dried over $Na_2SO_4$ and solvent was evaporated under reduced pressure to obtain crude compound. The crude compound was purified by column chromatography (silica gel, 100-200 mesh) to afford 250 mg (46% yield) of the title compound as an off-white solid. The structure of the compound was further confirmed by NOE (data not shown) and $^{13}$C NMR experiments.

$^1$H NMR (400 MHz, CDCl$_3$) δ: 6.52 (1H, d, J=2.52), 6.15 (1H, d, J=2.4 Hz), 3.91 (3H, s), 3.78 (3H, s), 3.62 (3H, s); $^{13}$C NMR (400 MHz, CDCl$_3$) δ: 166.01, 164.41, 162.48, 138.35, 105.62, 99.91, 55.62, 52.99, 32.80.

Step 4: 4-Methoxy-1-methyl-6-oxo-1,6-dihydropyridine-2-carboxylic acid

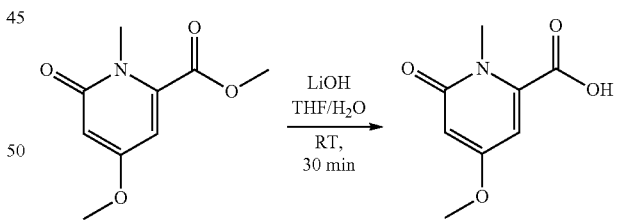

Lithium hydroxide monohydrate (107 mg, 2.53 mmol) was added at 0° C. to a stirred solution of methyl 4-methoxy-1-methyl-6-oxo-1,6-dihydropyridine-2-carboxylate (250 mg, 1.269 mmol) in THF (9 mL) and water (3 mL). The reaction mixture was stirred at room temperature for 30 min. After completion of reaction, solvent was distilled out, the residue was diluted with water (5 mL) and pH was adjusted to 4-5 using 1N HCl. The aqueous layer was extracted with ethyl acetate (2×20 mL). The combined organic layer washed with water (1×10 mL) and brine (10 mL), dried over anhydrous $Na_2SO_4$ and concentrated under reduced pressure to afford 100 mg (43% yield) of the title compound as an off-white solid.

Step 5: 4-Methoxy-1-methyl-6-oxo-1,6-dihydropyridine-2-carboxylic acid N'-(4-fluorophenyl)-hydrazide

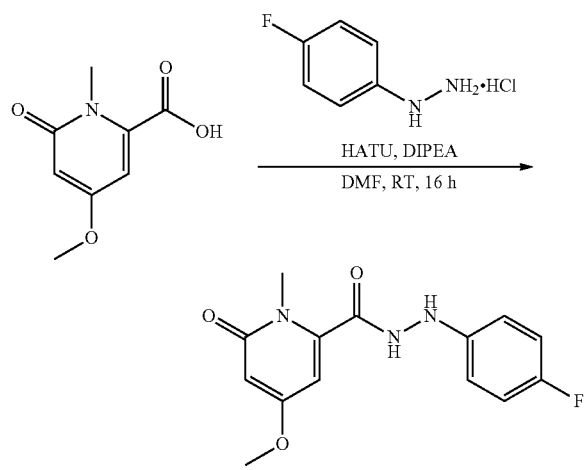

DIPEA (0.3 mL, 1.639 mmol), HATU (311 mg, 0.819 mmol) and 4-fluorophenylhydrazine hydrochloride (97 mg, 0.601 mmol) were added at 0° C. under nitrogen to a stirred solution of 4-methoxy-1-methyl-6-oxo-1,6-dihydropyridine-2-carboxylic acid (100 mg, 0.546 mmol) in DMF (5 mL). The reaction mixture was stirred at room temperature for 16 h, quenched with ice-water (5 mL) and extracted with ethyl acetate (2×15 mL). The combined organic layer was washed with water (1×10 mL), brine solution (10 mL), dried over anhydrous $Na_2SO_4$ and concentrated under reduced pressure. The crude compound was purified by column chromatography (silica gel, 100-200 mesh) to afford 40 mg (25% yield) of the title compound as an off-white solid $^1$H NMR (400 MHz, DMSO-d6) δ: 10.59 (1H, d, J=2.68), 8.01 (1H, d, J=2.72 Hz), 7.01 (2H, t, J=8.84 Hz), 6.85-6.79 (2H, m), 6.2 (1H, d, J=2.56 Hz), 5.92 (1H, d, J=2.56), 3.74 (3H, s), 3.28 (3H, s); LC-MS m/z (M–H): 290.

Example 22

Antimicrobial Activity

The products of the present invention were tested for their activity against *A. baumannii* as well as against the following bacteria: *Staphylococcus aureus* (*S. aureus*), *Streptococcus pneumoniae* (*S. pneumoniae*), *Enterococcus faecium* (*E. faecium*), *Pseudomonas aeruginosa* (*P. aeruginosa*), *Klebsiella pneumoniae* (*K. pneumoniae*), *Enterobacter aerogenes* (*E. aerogenes*) and *Escherichia coli* (*E. coli*).

Minimal inhibitory concentrations (MICs) were determined using a standard microtiter dilution method, according to the Clinical and Laboratory Standards Institute (CLSI) procedures, in particular according to M07-A9: "Methods for Dilution Antimicrobial Susceptibility Tests for Bacteria That Grow Aerobically; Approved Standard—Ninth Edition".

Briefly, compounds were dissolved with dimethyl sulfoxide (DMSO) at 12.8 mg/mL. Serial two-fold dilutions of compounds were performed in DMSO and 1 µl of each dilution were transferred into microtiter culture plates, followed by 100 µl of inoculated culture media to give a final microorganism concentration of 5×10$^5$ colony-forming units/mL. Plates were incubated at 37° C. for 24 hours and MICs determined as the lowest compound concentration that inhibited growth. Media used in determinations were Cation adjusted Mueller-Hinton Broth for all the microorganisms except for *S. pneumoniae* and *E. faecium* whose culture media were supplemented with 2.5% of lysed horse blood. Incubations were performed at air atmosphere except *S. pneumoniae* cultures that were incubated with 5% $CO_2$ atmosphere.

The results are given in Tables 1-4.

TABLE 1

| Bacteria | MIC (µg/mL) | | | | | |
|---|---|---|---|---|---|---|
| | Ex. 1 | Ex. 2 | Ex. 3 | Ex. 4 | Ex. 5 | Ex. 6 |
| A. baumannii | 0.5 | 1 | <0.25 | 1 | 0.25 | <0.25 |
| S. aureus | >128 | >128 | >128 | >128 | >128 | >128 |
| S. pneumoniae | >128 | >128 | >128 | >128 | >128 | >128 |
| E. faecium | >128 | >128 | >128 | >128 | >128 | >128 |
| P. aeruginosa | >128 | >128 | >128 | >128 | >128 | >128 |
| K. pneumoniae | >128 | >128 | >128 | >128 | >128 | >128 |
| E. aerogenes | >128 | >128 | >128 | >128 | >128 | >128 |
| E. coli | 64 | >128 | >128 | >128 | >128 | >128 |

TABLE 2

| Bacteria | MIC (µg/mL) | | | | | |
|---|---|---|---|---|---|---|
| | Ex. 7 | Ex. 8 | Ex. 9 | Ex. 10 | Ex. 11 | Ex. 12 |
| A. baumannii | 0.25 | 0.25 | 0.25 | 0.25 | 0.5 | 0.25 |
| S. aureus | >128 | >128 | >128 | >128 | >128 | >128 |
| S. pneumoniae | >128 | >128 | >128 | >128 | >128 | >128 |
| E. faecium | >128 | >128 | >128 | >128 | >128 | >128 |
| P. aeruginosa | >128 | >128 | >128 | >128 | >128 | >128 |
| K. pneumoniae | >128 | >128 | >128 | >128 | >128 | >128 |
| E. aerogenes | >128 | >128 | >128 | >128 | >128 | >128 |
| E. coli | >128 | >128 | >128 | >128 | >128 | >128 |

TABLE 3

| Bacteria | MIC (µg/mL) | | | | | |
|---|---|---|---|---|---|---|
| | Ex. 13 | Ex. 14 | Ex. 15 | Ex. 16 | Ex. 17 | Ex. 18 |
| A. baumannii | 0.5 | 0.25 | 0.5 | 0.5 | 0.5 | 0.25 |
| S. aureus | >128 | >128 | >128 | >128 | >128 | >128 |
| S. pneumoniae | >128 | >128 | >128 | >128 | >128 | >128 |
| E. faecium | >128 | >128 | >128 | >128 | >128 | >128 |
| P. aeruginosa | >128 | >128 | >128 | >128 | >128 | >128 |
| K. pneumoniae | >128 | >128 | >128 | >128 | >128 | >128 |
| E. aerogenes | >128 | >128 | >128 | >128 | >128 | >128 |
| E. coli | >128 | >128 | >128 | >128 | >128 | >128 |

TABLE 4

| Bacteria | MIC (µg/mL) | | |
|---|---|---|---|
| | Ex. 19 | Ex. 20 | Ex. 21 |
| A. baumannii | 0.25 | 64 | 0.25 |
| S. aureus | >128 | >128 | >128 |
| S. pneumoniae | >128 | >128 | >128 |
| E. faecium | >128 | >128 | >128 |
| P. aeruginosa | >128 | >128 | >128 |
| K. pneumoniae | >128 | >128 | >128 |
| E. aerogenes | >128 | >128 | >128 |
| E. coli | >128 | >128 | >128 |

As shown in Tables 1-4, compounds of formula (I) according to the present invention are highly effective antibacterials against *A. baumannii*, with MIC values of 1 or less for almost all compounds tested. Surprisingly, all the compounds showed a great selectivity in the activity against *A. baumannii*, since they were virtually inactive against the other bacteria tested.

The invention claimed is:

1. A compound of formula (I):

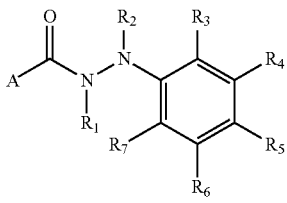

or a pharmaceutically acceptable salt, or solvate thereof, wherein

A is a radical selected from $A_1$, $A_2$, $A_3$ and $A_4$;

$A_1$ is

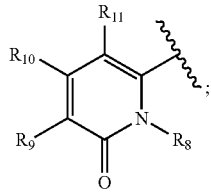

$A_2$ is

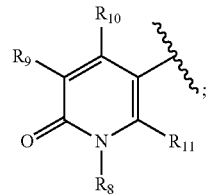

$A_3$ is

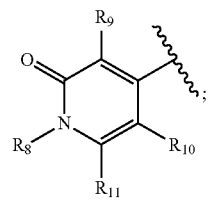

$A_4$ is

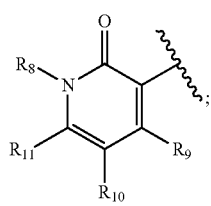

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$;

$R_8$ is selected from $C_{1-6}$alkyl, $C_{2-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl, Ph $C_{1-4}$alkyl and —$C_{1-4}$alkyl-$CONR_{12}R_{13}$;

$R_9$, $R_{10}$ and $R_{11}$ are independently selected from hydrogen, $C_{1-6}$alkyl, $C_{3-6}$cycloalkyl$C_{0-4}$alkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$; and each $R_{12}$ and $R_{13}$ are independently selected from hydrogen and $C_{1-4}$alkyl;

with the proviso that the following products are excluded:
1-methyl-6-oxo-1,6-dihydro-pyridine-2-carboxylic acid N'-phenylhydrazide,
1-benzyl-2-oxo-1,2-dihydro-pyridine-3-carboxylic acid N'-(2-(trifluoromethyl)phenyl)-hydrazide,
1-benzyl-4,6-dimethyl-2-oxo-1,2-dihydro-pyridine-3-carboxylic acid N'-phenyl-hydrazide,
1-methyl-2-oxo-1,2-dihydro-pyridine-4-carboxylic acid N'-(2,4,6-trichlorophenyl)-hydrazide,
1-((3-methylphenyl)methyl)-2-oxo-1,2-dihydro-pyridine-3-carboxylic acid N'-(3-(trifluoromethyl)phenyl)-hydrazide and
1-((2-chlorophenyl)methyl)-6-oxo-1,6-dihydro-pyridine-3-carboxylic acid N'-phenyl-N'-methyl-hydrazide.

2. A compound according to claim 1, wherein $R_8$ is selected from $C_{1-6}$alkyl, $C_{2-6}$alkenyl, $C_{2-6}$alkynyl, halo $C_{1-6}$alkyl, hydroxy$C_{1-4}$alkyl, $C_{1-4}$alkoxy, $C_{1-4}$alkoxy $C_{1-4}$alkyl, $C_{3-6}$cycloalkyl$C_{1-4}$alkyl and Ph$C_{1-4}$alkyl.

3. A compound according to claim 1, wherein A is $A_1$.

4. A compound according claim 1, wherein $R_1$ and $R_2$ are independently selected from hydrogen and $C_{1-4}$alkyl.

5. A compound according to claim 4, wherein $R_1$ and $R_2$ are hydrogen.

6. A compound according to claim 4, wherein one of $R_1$ and $R_2$ is hydrogen and the other is $C_{1-4}$alkyl.

7. A compound according to claim 4, wherein $R_1$ and $R_2$ are $C_{1-4}$alkyl.

8. A compound according to claim 1 wherein $R_3$, $R_4$, $R_5$, $R_6$ and $R_7$ are independently selected from hydrogen, halogen, —OH, $C_{1-6}$alkyl and $C_{1-4}$alkoxy.

9. A compound according to claim 8, wherein $R_5$ is selected from halogen, —OH, $C_{1-6}$alkyl and $C_{1-4}$alkoxy, and $R_3$, $R_4$, $R_6$ and $R_7$ are independently selected from hydrogen and halogen.

10. A compound according to claim 8, wherein $R_5$ is selected from halogen, —OH, $C_{1-6}$alkyl and $C_{1-4}$alkoxy, and $R_3$, $R_4$, $R_6$ and $R_7$ are hydrogen.

11. A compound according to claim 1, wherein $R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl.

12. A compound according to claim 1, wherein $R_8$ is selected from $C_{1-4}$alkyl, $C_{2-4}$alkynyl, halo$C_{1-4}$alkyl, $C_{1-4}$alkoxy$C_{1-4}$alkyl, $C_{3-6}$cycloalkyl$C_{1-4}$alkyl, Ph$C_{1-4}$alkyl and —$C_{1-4}$alkyl-$CONR_{12}R_{13}$.

13. A compound according to claim 12, wherein $R_8$ is selected from $C_{1-4}$alkyl, $C_{2-4}$alkynyl, halo$C_{1-4}$alkyl, $C_{3-6}$cycloalkyl$C_{1-4}$alkyl and Ph$C_{1-4}$alkyl.

14. A compound according to claim 1, wherein $R_9$, $R_{10}$ and $R_{11}$ are independently selected from hydrogen, $C_{1-4}$alkyl and $C_{1-4}$alkoxy.

15. A compound according to claim 14, wherein $R_9$, $R_{10}$ and $R_{11}$ are independently selected from hydrogen and $C_{1-4}$alkoxy.

16. A compound according to claim 14, wherein $R_9$, $R_{10}$ and $R_{11}$ are hydrogen.

17. A compound according to claim 1, which is selected from the group consisting of:
- 1-methyl-6-oxo-1,6-dihydropyridine-2-carboxylic acid, N'-(4-fluorophenyl)-hydrazide;
- 1-ethyl-6-oxo-1,6-dihydropyridine-2-carboxylic acid, N'-(4-fluorophenyl)-hydrazide;
- 1-(2-methoxyethyl)-6-oxo-1,6-dihydropyridine-2-carboxylic acid, N'-(4-fluorophenyl)-hydrazide;
- 1-difluoromethyl-6-oxo-1,6-dihydropyridine-2-carboxylic acid, N'-(4-fluorophenyl)-hydrazide;
- 1-benzyl-6-oxo-1,6-dihydropyridine-2-carboxylic acid, N'-(4-fluorophenyl)-hydrazide;
- 1-cyclopropylmethyl-6-oxo-1,6-dihydropyridine-2-carboxylic acid, N'-(4-fluorophenyl)-hydrazide;
- 4-methoxy-1-methyl-6-oxo-1,6-dihydropyridine-2-carboxylic acid, N'-(4-fluorophenyl)-hydrazide;
- 1-(prop-2-yn-1-yl)-6-oxo-1,6-dihydropyridine-2-carboxylic acid, N'-(4-fluorophenyl)-hydrazide;
- 5-ethyl-1-methyl-6-oxo-1,6-dihydropyridine-2-carboxylic acid, N'-(4-fluorophenyl)-hydrazide;
- 6-oxo-1-(2,2,2-trifluoroethyl)-1,6-dihydropyridine-2-carboxylic acid, N'-(4-fluorophenyl)-hydrazide;
- 1-methyl-6-oxo-1,6-dihydropyridine-2-carboxylic acid, N'-(4-methoxyphenyl)-hydrazide;
- 1-methyl-6-oxo-1,6-dihydropyridine-2-carboxylic acid, N'-(4-chlorophenyl)-hydrazide;
- 1-methyl-6-oxo-1,6-dihydropyridine-2-carboxylic acid, N'-(4-methylphenyl)-hydrazide;
- 1-methyl-6-oxo-1,6-dihydropyridine-2-carboxylic acid, N'-(2,4-difluorophenyl)-hydrazide;
- 1-methyl-6-oxo-1,6-dihydropyridine-2-carboxylic acid, N'-(2,6-difluorophenyl)-hydrazide;
- 1-methyl-6-oxo-1,6-dihydropyridine-2-carboxylic acid, N'-(4-fluorophenyl)-N,N'-dimethyl-hydrazide;
- 1-methyl-6-oxo-1,6-dihydropyridine-2-carboxylic acid, N'-(4-fluorophenyl)-N'-methyl-hydrazide;
- 1-methyl-6-oxo-1,6-dihydropyridine-2-carboxylic acid, N'-(4-fluorophenyl)-N-methyl-hydrazide;
- 1-(2-(dimethylamino)-2-oxoethyl)-6-oxo-1,6-dihydropyridine-2-carboxylic acid, N'-(4-fluorophenyl)-hydrazide;
- 1-(2-amino-2-oxoethyl)-6-oxo-1,6-dihydropyridine-2-carboxylic acid, N'-(4-fluorophenyl)-hydrazide;
- 1-ethyl-2-oxo-1,2-dihydropyridine-3-carboxylic acid, N'-(4-fluorophenyl)-hydrazide;
- 1-methyl-2-oxo-1,2-dihydropyridine-3-carboxylic acid, N'-(4-fluorophenyl)-hydrazide;
- 1-methyl-2-oxo-1,2-dihydropyridine-4-carboxylic acid, N'-(4-fluorophenyl)-hydrazide; and
- 1-methyl-6-oxo-1,6-dihydropyridine-3-carboxylic acid, N'-(4-fluorophenyl)-hydrazide;

or a pharmaceutically acceptable salt, or solvate thereof.

18. A method for manufacturing a medicament, said method comprising:
preparing the medicament comprising a compound of formula (I):

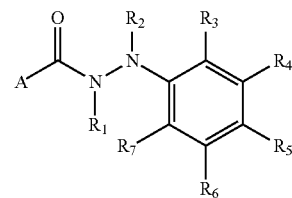

or a pharmaceutically acceptable salt, or solvate thereof, wherein

A is a radical selected from $A_1$, $A_2$, $A_3$ and $A_4$;

$A_1$ is

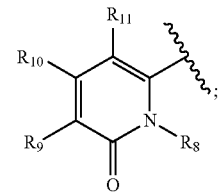

$A_2$ is

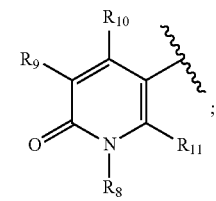

$A_3$ is

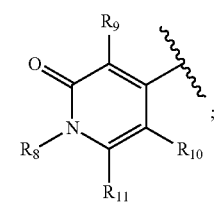

$A_4$ is

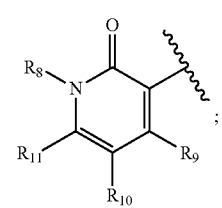

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —NR$_{12}$R$_{13}$, —N(R$_{12}$)COR$_{13}$, —N(R$_{12}$)SO$_2$R$_{13}$, haloC$_{1-6}$alkyl, hydroxyC$_{1-6}$alkyl, C$_{1-4}$alkoxy, C$_{1-4}$alkoxyC$_{1-6}$alkyl, —COOR$_{12}$, —CN, —CONR$_{12}$R$_{13}$, —SO$_2$—C$_{1-4}$alkyl, —SO$_2$—O—C$_{1-4}$alkyl and —SO$_2$—NR$_{12}$R$_{13}$;

R$_8$ is selected from C$_{1-6}$alkyl, C$_{2-6}$alkenyl, C$_{2-6}$alkynyl, haloC$_{1-6}$alkyl, hydroxyC$_{1-4}$alkyl, C$_{1-4}$alkoxy, C$_{1-4}$alkoxyC$_{1-4}$alkyl, C$_{3-6}$cycloalkylC$_{1-4}$alkyl, Ph C$_{1-4}$alkyl and —C$_{1-4}$alkyl-CONR$_{12}$R$_{13}$;

R$_9$, R$_{10}$ and R$_{11}$ are independently selected from hydrogen, C$_{1-6}$alkyl, C$_{3-6}$cycloalkylC$_{0-4}$alkyl, —NR$_{12}$R$_{13}$, —N(R$_{12}$)COR$_{13}$, —N(R$_{12}$)SO$_2$R$_{13}$, haloC$_{1-6}$alkyl, hydroxyC$_{1-6}$alkyl, C$_{1-4}$alkoxy, C$_{1-4}$alkoxyC$_{1-6}$alkyl, —COOR$_{12}$, —CN, —CONR$_{12}$R$_{13}$, —SO$_2$—C$_{1-4}$alkyl, —SO$_2$—O—C$_{1-4}$alkyl and —SO$_2$—NR$_{12}$R$_{13}$; and each R$_{12}$ and R$_{13}$ are independently selected from hydrogen and C$_{1-4}$alkyl.

19. The method for manufacturing a medicament according to claim 18, wherein A is A$_1$, R$_1$ and R$_2$ are independently selected from hydrogen and C$_{1-4}$alkyl, R$_3$, R$_4$, R$_5$, R$_6$ and R$_7$ are independently selected from hydrogen, halogen, —OH, C$_{1-6}$alkyl and C$_{1-4}$alkoxy, R$_8$ is selected from C$_{1-6}$-alkyl, C$_{2-6}$alkenyl, C$_{2-6}$alkynyl, haloC$_{1-6}$alkyl, hydroxyC$_{1-4}$alkyl, C$_{1-4}$alkoxy, C$_{1-4}$alkoxyC$_{1-4}$alkyl, C$_{3-6}$cycloalkylC$_{1-4}$alkyl and PhC$_{1-4}$alkyl, and —C$_{1-4}$alkyl-CONR$_{12}$R$_{13}$, R$_9$, R$_{10}$ and R$_{11}$ are independently selected from hydrogen, C$_{1-4}$alkyl and C$_{1-4}$alkoxy, or wherein the compound of formula (I) is selected from the group consisting of:

1-methyl-6-oxo-1,6-dihydropyridine-2-carboxylic acid, N'-(4-fluorophenyl)-hydrazide;
1-ethyl-6-oxo-1,6-dihydropyridine-2-carboxylic acid, N'-(4-fluorophenyl)-hydrazide;
1-(2-methoxyethyl)-6-oxo-1,6-dihydropyridine-2-carboxylic acid, N'-(4-fluorophenyl)-hydrazide;
1-difluoromethyl-6-oxo-1,6-dihydropyridine-2-carboxylic acid, N'-(4-fluorophenyl)-hydrazide;
1-benzyl-6-oxo-1,6-dihydropyridine-2-carboxylic acid, N'-(4-fluorophenyl)-hydrazide;
1-cyclopropylmethyl-6-oxo-1,6-dihydropyridine-2-carboxylic acid, N'-(4-fluorophenyl)-hydrazide;
4-methoxy-1-methyl-6-oxo-1,6-dihydropyridine-2-carboxylic acid, N'-(4-fluorophenyl)-hydrazide;
1-(prop-2-yn-1-yl)-6-oxo-1,6-dihydropyridine-2-carboxylic acid, N'-(4-fluorophenyl)-hydrazide;
5-ethyl-1-methyl-6-oxo-1,6-dihydropyridine-2-carboxylic acid, N'-(4-fluorophenyl)-hydrazide;
6-oxo-1-(2,2,2-trifluoroethyl)-1,6-dihydropyridine-2-carboxylic acid, N'-(4-fluorophenyl)-hydrazide;
1-methyl-6-oxo-1,6-dihydropyridine-2-carboxylic acid, N'-(4-methoxyphenyl)-hydrazide;
1-methyl-6-oxo-1,6-dihydropyridine-2-carboxylic acid, N'-(4-chlorophenyl)-hydrazide;
1-methyl-6-oxo-1,6-dihydropyridine-2-carboxylic acid, N'-(4-methylphenyl)-hydrazide;
1-methyl-6-oxo-1,6-dihydropyridine-2-carboxylic acid, N'-(2,4-difluorophenyl)-hydrazide;
1-methyl-6-oxo-1,6-dihydropyridine-2-carboxylic acid, N'-(2,6-difluorophenyl)-hydrazide;
1-methyl-6-oxo-1,6-dihydropyridine-2-carboxylic acid, N'-(4-fluorophenyl)-N,N'-dimethyl-hydrazide;
1-methyl-6-oxo-1,6-dihydropyridine-2-carboxylic acid, N'-(4-fluorophenyl)-N'-methyl-hydrazide;
1-methyl-6-oxo-1,6-dihydropyridine-2-carboxylic acid, N'-(4-fluorophenyl)-N-methyl-hydrazide;
1-(2-(dimethylamino)-2-oxoethyl)-6-oxo-1,6-dihydropyridine-2-carboxylic acid, N'-(4-fluorophenyl)-hydrazide;
1-(2-amino-2-oxoethyl)-6-oxo-1,6-dihydropyridine-2-carboxylic acid, N'-(4-fluorophenyl)-hydrazide;
1-ethyl-2-oxo-1,2-dihydropyridine-3-carboxylic acid, N'-(4-fluorophenyl)-hydrazide;
1-methyl-2-oxo-1,2-dihydropyridine-3-carboxylic acid, N'-(4-fluorophenyl)-hydrazide;
1-methyl-2-oxo-1,2-dihydropyridine-4-carboxylic acid, N'-(4-fluorophenyl)-hydrazide; and
1-methyl-6-oxo-1,6-dihydropyridine-3-carboxylic acid, N'-(4-fluorophenyl)-hydrazide;
or a pharmaceutically acceptable salt, or solvate thereof.

20. A method for the manufacture of an antibacterial agent, said method comprising:

preparing the antibacterial agent comprising a compound of formula (I):

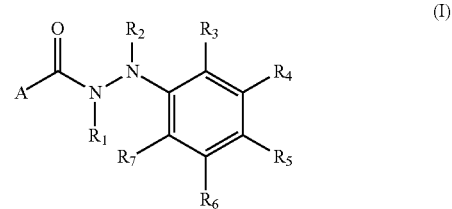

or a pharmaceutically acceptable salt, or solvate thereof, wherein

A is a radical selected from A$_1$, A$_2$, A$_3$ and A$_4$;

A$_1$ is

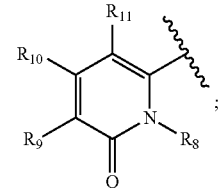

A$_2$ is

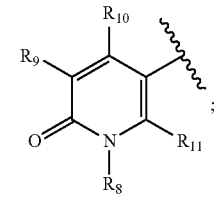

A$_3$ is

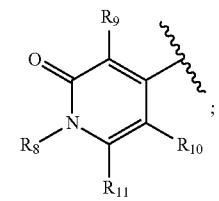

A4 is

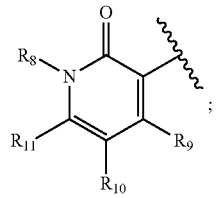

R₁ and R₂ are independently selected from hydrogen, C₁₋₄alkyl, haloC₁₋₄alkyl, hydroxyC₁₋₄alkyl and C₁-4alkoxyC₁₋₄alkyl;

R₃, R₄, R₅, R₆ and R₇ are independently selected from hydrogen, —OH, halogen, C₁₋₆alkyl, C₃₋₆cycloalkyl, —NR₁₂R₁₃, —N(R₁₂)COR₁₃, —N(R₁₂)SO₂R₁₃, haloC₁₋₆alkyl, hydroxyC₁₋₆alkyl, C₁₋₄alkoxy, C₁₋₄alkoxyC₁₋₆alkyl, —COOR₁₂, —CN, —CONR₁₂R₁₃, —SO₂—C₁₋₄alkyl, —SO₂—O—C₁₋₄alkyl and —SO₂—NR₁₂R₁₃;

R₈ is selected from C₁₋₆alkyl, C₂₋₆alkenyl, C₂₋₆alkynyl, haloC₁₋₆alkyl, hydroxyC₁₋₄alkyl, C₁₋₄alkoxy, C₁₋₄alkoxyC₁₋₄alkyl, C₃₋₆cycloalkylC₁₋₄alkyl, Ph C₁₋₄alkyl and —C₁₋₄alkyl-CONR₁₂R₁₃;

R₉, R₁₀ and R₁₁ are independently selected from hydrogen, C₁₋₆alkyl, C₃₋₆cycloalkylC₀₋₄alkyl, —NR₁₂R₁₃, —N(R₁₂)COR₁₃, —N(R₁₂)SO₂R₁₃, haloC₁₋₆alkyl, hydroxyC₁₋₆alkyl, C₁₋₄alkoxy, C₁₋₄alkoxyC₁₋₆alkyl, —COOR₁₂, —CN, —CONR₁₂R₁₃, —SO₂—C₁₋₄alkyl, —SO₂—O—C₁₋₄alkyl and —SO₂—NR₁₂R₁₃; and each R₁₂ and R₁₃ are independently selected from hydrogen and C₁₋₄alkyl.

21. The method according to claim 18, wherein
A is A₁,
R₁ and R₂ are independently selected from hydrogen and C₁₋₄alkyl,
R₃, R₄, R₅, R₆ and R₇ are independently selected from hydrogen, halogen, —OH, C₁₋₆alkyl and C₁₋₄alkoxy,
R₈ is selected from C₁₋₆alkyl, C₂₋₆alkenyl, C₂₋₆alkynyl, haloC₁₋₆alkyl, hydroxyC₁₋₄alkyl, C₁₋₄alkoxy, C₁₋₄alkoxyC₁₋₄alkyl, C₃₋₆cycloalkylC₁₋₄alkyl and PhC₁₋₄alkyl, and —C₁₋₄ alkyl-CONR₁₂R₁₃,
R₉, R₁₀ and R₁₁ are independently selected from hydrogen, C₁₋₄alkyl and C₁₋₄alkoxy, or wherein the compound of formula (I) is selected from the group consisting of:

1-methyl-6-oxo-1,6-dihydropyridine-2-carboxylic acid, N'-(4-fluorophenyl)-hydrazide;
1-ethyl-6-oxo-1,6-dihydropyridine-2-carboxylic acid, N'-(4-fluorophenyl)-hydrazide;
1-(2-methoxyethyl)-6-oxo-1,6-dihydropyridine-2-carboxylic acid, N'-(4-fluorophenyl)-hydrazide;
1-difluoromethyl-6-oxo-1,6-dihydropyridine-2-carboxylic acid, N'-(4-fluorophenyl)-hydrazide;
1-benzyl-6-oxo-1,6-dihydropyridine-2-carboxylic acid, N'-(4-fluorophenyl)-hydrazide;
1-cyclopropylmethyl-6-oxo-1,6-dihydropyridine-2-carboxylic acid, N'-(4-fluorophenyl)-hydrazide;
4-methoxy-1-methyl-6-oxo-1,6-dihydropyridine-2-carboxylic acid, N'-(4-fluorophenyl)-hydrazide;
1-(prop-2-yn-1-yl)-6-oxo-1,6-dihydropyridine-2-carboxylic acid, N'-(4-fluorophenyl)-hydrazide;
5-ethyl-1-methyl-6-oxo-1,6-dihydropyridine-2-carboxylic acid, N'-(4fluorophenyl)-hydrazide;
6-oxo-1-(2,2,2-trifluoroethyl)-1,6-dihydropyridine-2-carboxylic acid, N'-(4-fluorophenyl)-hydrazide;
1-methyl-6-oxo-1,6-dihydropyridine-2-carboxylic acid, N'-(4-methoxyphenyl)-hydrazide;
1-methyl-6-oxo-1,6-dihydropyridine-2-carboxylic acid, N'-(4-chlorophenyl)-hydrazide;
1-methyl-6-oxo-1,6-dihydropyridine-2-carboxylic acid, N'-(4-methylphenyl)-hydrazide:
1-methyl-6-oxo-1,6-dihydropyridine-2-carboxylic acid, N'-(2,4-difluorophenyl)-hydrazide;
1-methyl-6-oxo-1,6-dihydropyridine-2-carboxylic acid, N'-(2,6-difluorophenyl)-hydrazide;
1-methyl-6-oxo-1,6-dihydropyridine-2-carboxylic acid, N'-(4-fluorophenyl)-N,N'-dimethyl-hydrazide;
1-methyl-6-oxo-1,6-dihydropyridine-2-carboxylic acid, N'-(4-fluorophenyl)-N'-methyl-hydrazide:
1-methyl-6-oxo-1,6-dihydropyridine-2-carboxylic acid, N'-(4-fluorophenyl)-N-methyl-hydrazide;
1-(2-(dimethylamino)-2-oxoethyl)-6-oxo-1,6-dihydropyridine-2-carboxylic acid, N'-(4-fluorophenyl)-hydrazide;
1-(2-amino-2-oxoethyl)-6-oxo-1,6-dihydropyridine-2-carboxylic acid, N'-(4-fluorophenyl)-hydrazide;
1-ethyl-2-oxo-1,2-dihydropyridine-3-carboxylic acid, N'-(4-fluorophenyl)-hydrazide;
1-methyl-2-oxo-1,2-dihydropyridine-3-carboxylic acid, N'-(4-fluorophenyl)-hydrazide;
1-methyl-2-oxo-1,2-dihydropyridine-4-carboxylic acid, N'-(4-fluorophenyl)-hydrazide; and
1-methyl-6-oxo-1,6-dihydropyridine-3-carboxylic acid, N'-(4-fluorophenyl)-hydrazide;

or a pharmaceutically acceptable salt, or solvate thereof.

22. A method for the treatment or prevention of bacterial infections in a subject in need thereof, comprising administering an effective amount of a compound of formula (I):

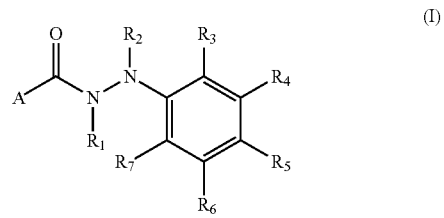

(I)

or a pharmaceutically acceptable salt, or solvate thereof, wherein
A is a radical selected from A₁, A₂ and A₃;
A₁ is

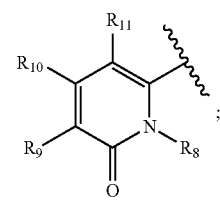

A₂ is

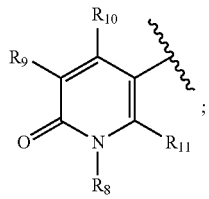

A₃ is

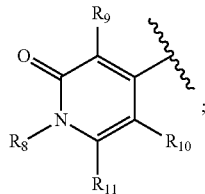

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —NR$_{12}$R$_{13}$, —N(R$_{12}$)COR$_{13}$, —N(R$_{12}$)SO$_2$R$_{13}$, halo$C_{1-6}$alkyl, hydroxy$C_{1-6}$alkyl, $C_{1-4}$alkoxy, $C_{1-4}$alkoxy$C_{1-6}$alkyl, —COOR$_{12}$, —CN, —CONR$_{12}$R$_{13}$, —SO$_2$—$C_{1-4}$alkyl, —SO$_2$—O—$C_{1-4}$alkyl and —SO$_2$—NR$_{12}$R$_{13}$;

$R_8$ is selected from $C_{1-6}$alkyl, $C_{2-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl, Ph $C_{1-4}$alkyl and —$C_{1-4}$alkyl-CONR$_{12}$R$_{13}$;

$R_9$, $R_{10}$ and $R_{11}$ are independently selected from hydrogen, $C_{1-6}$alkyl, $C_{3-6}$cycloalkyl$C_{0-4}$alkyl, —NR$_{12}$R$_{13}$, —N(R$_{12}$)COR$_{13}$, —N(R$_{12}$)SO$_2$R$_{13}$, halo$C_{1-6}$alkyl, hydroxy$C_{1-6}$alkyl, $C_{1-4}$alkoxy, $C_{1-4}$alkoxy$C_{1-6}$alkyl, —COOR$_{12}$, —CN, —CONR$_{12}$R$_{13}$, —SO$_2$—$C_{1-4}$alkyl, —SO$_2$—O—$C_{1-4}$alkyl and —SO$_2$—NR$_{12}$R$_{13}$; and each $R_{12}$ and $R_{13}$ are independently selected from hydrogen and $C_{1-4}$alkyl.

23. Method according to claim 22, wherein

A is $A_1$, $R_1$ and $R_2$ are independently selected from hydrogen and $C_{1-4}$alkyl, $R_3$, $R_4$, $R_5$, $R_6$ and $R_7$ are independently selected from hydrogen, halogen, —OH, $C_{1-6}$alkyl and $C_{1-4}$alkoxy, $R_8$ is selected from $C_{1-6}$alkyl, $C_{1-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl and Ph$C_{1-4}$alkyl, and —$C_{1-4}$alkyl-CONR$_{12}$R$_{13}$, $R_9$, $R_{10}$ and $R_{11}$ are independently selected from hydrogen, $C_{1-4}$alkyl and $C_{1-4}$alkoxy, or wherein the compound of formula (I) is selected from the group consisting of:

1-methyl-6-oxo-1,6-dihydropyridine-2-carboxylic acid, N'-(4-fluorophenyl)-hydrazide;
1-ethyl-6-oxo-1,6-dihydropyridine-2-carboxylic acid, N'-(4-fluorophenyl)-hydrazide;
1-(2-methoxyethyl)-6-oxo-1,6-dihydropyridine-2-carboxylic acid, N'-(4-fluorophenyl)-hydrazide;
1-difluoromethyl-6-oxo-1,6-dihydropyridine-2-carboxylic acid, N'-(4-fluorophenyl)-hydrazide;
1-benzyl-6-oxo-1,6-dihydropyridine-2-carboxylic acid, N'-(4-fluorophenyl)-hydrazide;
1-cyclopropylmethyl-6-oxo-1,6-dihydropyridine-2-carboxylic acid, N'-(4-fluorophenyl)-hydrazide;
4-methoxy-1-methyl-6-oxo-1,6-dihydropyridine-2-carboxylic acid, N'-(4-fluorophenyl)-hydrazide;
1-(prop-2-yn-1-yl)-6-oxo-1,6-dihydropyridine-2-carboxylic acid, N-4-fluorophenyl)-hydrazide;
5-ethyl-1-methyl-6-oxo-1,6-dihydropyridine-2-carboxylic acid, N'-(4-fluorophenyl)-hydrazide;
6-oxo-1-(2,2,2-trifluoroethyl)-1,6-dihydropyridine-2-carboxylic acid, N'-(4-fluorophenyl)-hydrazide;
1-methyl-6-oxo-1,6-dihydropyridine-2-carboxylic acid, N'-(4-methoxyphenyl)-hydrazide;
1-methyl-6-oxo-1,6-dihydropyridine-2-carboxylic acid, N'-(4-chlorophenyl)-hydrazide;
1-methyl-6-oxo-1,6-dihydropyridine-2-carboxylic acid, N'-(4-methylphenyl)-hydrazide;
1-methyl-6-oxo-1,6-dihydropyridine-2-carboxylic acid, N'-(2,4-difluorophenyl)-hydrazide;
1-methyl-6-oxo-1,6-dihydropyridine-2-carboxylic acid, N'-(2,6-difluorophenyl)-hydrazide;
1-methyl-6-oxo-1,6-dihydropyridine-2-carboxylic acid, N'-(4-fluorophenyl)-N,N'-dimethyl-hydrazide;
1-methyl-6-oxo-1,6-dihydropyridine-2-carboxylic acid, N'-(4-fluorophenyl)-N'-methyl-hydrazide;
1-methyl-6-oxo-1,6-dihydropyridine-2-carboxylic acid, N'-(4-fluorophenyl)-N-methyl-hydrazide;
1-(2-(dimethylamino)-2-oxoethyl)-6-oxo-1,6-dihydropyridine-2-carboxylic acid, N'-(4-fluorophenyl)-hydrazide;
1-(2-amino-2-oxoethyl)-6-oxo-1,6-dihydropyridine-2-carboxylic acid, N'-(4-fluorophenol)-hydrazide;
1-ethyl-2-oxo-1,2-dihydropyridine-3-carboxylic acid, N'-(4-fluorophenyl)-hydrazide;
1-methyl-2-oxo-1,2-dihydropyridine-3-carboxylic acid, N'-(4-fluorophenyl)-hydrazide;
1-methyl-2-oxo-1,2-dihydropyridine-4-carboxylic acid, N'-(4-fluorophenyl)-hydrazide; and
1-methyl-6-oxo-1,6-dihydropyridine-3-carboxylic acid, N'-(4-fluorophenyl)-hydrazide;

or a pharmaceutically acceptable salt, or solvate thereof.

24. The method according to claim 22, wherein the bacterial infections is *A. baumannii*.

25. A pharmaceutical composition comprising a compound of formula (I):

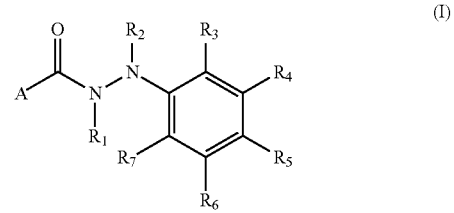

(I)

or a pharmaceutically acceptable salt, or solvate thereof, wherein

A is a radical selected from $A_1$, $A_2$ and $A_3$;

$A_1$ is

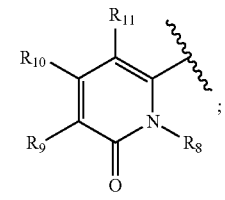

$A_2$ is

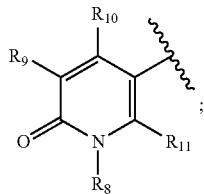

$A_3$ is

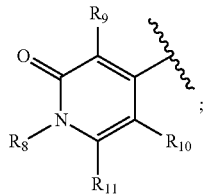

$R_1$ and $R_2$ are independently selected from hydrogen, $C_{1-4}$alkyl, halo$C_{1-4}$alkyl, hydroxy$C_{1-4}$alkyl and $C_{1-4}$alkoxy$C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$;

$R_8$ is selected from $C_{1-6}$alkyl, $C_{2-6}$alkenyl, $C_{2-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl, Ph $C_{1-4}$alkyl and —$C_{1-4}$alkyl-$CONR_{12}R_{13}$;

$R_9$, $R_{10}$ and $R_{11}$ are independently selected from hydrogen, $C_{1-6}$alkyl, $C_{3-6}$cycloalkyl$C_{0-4}$alkyl, —$NR_{12}R_{13}$, —$N(R_{12})COR_{13}$, —$N(R_{12})SO_2R_{13}$, halo$C_{1-6}$alkyl, hydroxy$C_{1-6}$alkyl, $C_{1-4}$alkoxy, $C_{1-4}$alkoxy$C_{1-6}$alkyl, —$COOR_{12}$, —CN, —$CONR_{12}R_{13}$, —$SO_2$—$C_{1-4}$alkyl, —$SO_2$—O—$C_{1-4}$alkyl and —$SO_2$—$NR_{12}R_{13}$; and each $R_{12}$ and $R_{13}$ are independently selected from hydrogen and $C_{1-4}$alkyl;

and at least one pharmaceutically acceptable excipient and/or carrier.

26. A pharmaceutical composition according to claim 25, wherein
A is $A_1$,
$R_1$ and $R_2$ are independently selected from hydrogen and $C_{1-4}$alkyl,
$R_3$, $R_4$, $R_5$, $R_6$ and $R_7$ are independently selected from hydrogen, halogen, —OH, $C_{1-6}$alkyl and $C_{1-4}$alkoxy,
$R_8$ is selected from $C_{1-6}$alkyl, $C_{1-6}$alkenyl, $C_{1-6}$alkynyl, halo$C_{1-6}$alkyl, hydroxy$C_{1-4}$alkyl, $C_{1-4}$alkoxy, $C_{1-4}$alkoxy$C_{1-4}$alkyl, $C_{3-6}$cycloalkyl$C_{1-4}$alkyl and Ph$C_{1-4}$alkyl, and —$C_{1-4}$alkyl-$CONR_{12}R_{13}$,
$R_9$, $R_{10}$ and $R_{11}$ are independently selected from hydrogen, $C_{1-4}$alkyl and $C_{1-4}$alkoxy, or wherein the compound of formula (I) is selected from the group consisting of:

1-methyl-6-oxo-1,6-dihydropyridine-2-carboxylic acid, N'-(4-fluorophenyl)-hydrazide;
1-ethyl-6-oxo-1,6-dihydropyridine-2-carboxylic acid, N'-(4-fluorophenyl)-hydrazide;
1-(2-methoxyethyl)-6-oxo-1,6-dihydropyridine-2-carboxylic acid, N'-(4-fluorophenyl)-hydrazide;
1-difluoromethyl-6-oxo-1,6-dihydropyridine-2-carboxylic acid, N'-(4-fluorophenyl)-hydrazide;
1-benzyl-6-oxo-1,6-dihydropyridine-2-carboxylic acid, N'-(4-fluorophenyl)-hydrazide;
1-cyclopropylmethyl-6-oxo-1,6-dihydropyridine-2-carboxylic acid, N'-(4-fluorophenyl)-hydrazide;
4-methoxy-1-methyl-6-oxo-1,6-dihydropyridine-2-carboxylic acid, N'-(4-fluorophenyl)-hydrazide;
1-(prop-2-yn-1-yl)-6-oxo-1,6-dihydropyridine-2-carboxylic acid, N'-(4-fluorophenyl)-hydrazide;
5-ethyl-1-methyl-6-oxo-1,6-dihydrouridine-2-carboxylic acid, N'-(4-fluorophenyl)-hydrazide;
6-oxo-1-(2,2,2-trifluoroethyl)-1,6-dihydropyridine-2-carboxylic acid, N'-(4-fluorophenyl)-hydrazide;
1-methyl-6-oxo-1,6-dihydropyridine-2-carboxylic acid, N'-(4-methoxyphenyl)-hydrazide;
1-methyl-6-oxo-1,6-dihydroppyridine-2-carboxylic acid, N'-(4-chlorophenyl)-hydrazide;
1-methyl-6-oxo-1,6-dihydropyridine-2-carboxylic acid, N'-(4-methylphenyl)-hydrazide;
1-methyl-6-oxo-1,6-dihydropyridine-2-carboxylic acid, N'-(2,4-difluorophenyl)-hydrazide;
1-methyl-6-oxo-1,6-dihydropyridine-2-carboxylic acid, N'-(2,6-difluorophenyl)-hydrazide;
1-methyl-6-oxo-1,6-dihydropyridine-2-carboxylic acid, N'-(4-fluorophenyl)-N,N'-dimethyl-hydrazide;
1-methyl-6-oxo-1,6-dihydropyridine-2-carboxylic acid, N'-(4-fluorophenvl)-N'-methyl-hydrazide;
1-methyl-6-oxo-1,6-dihydropyridine-2-carboxylic acid, N'-(4-fluorophenyl)-N-methyl-hydrazide;
1-(2-(dimethylamino)-2-oxoethyl)-6-oxo-1,6-dihydropyridine-2-carboxylic acid, N'-(4-fluorophenyl)-hydrazide;
1-(2-amino-2-oxoethyl)-6-oxo-1,6-dihydropyridine-2-carboxylic acid, N'-(4-fluorophenyl)-hydrazide;
1-ethyl-2-oxo-1,2-dihydropyridine-3-carboxylic acid, N'-(4-fluorophenyl)-hydrazide;
1-methyl-2-oxo-1,2-dihydropyridine-3-carboxylic acid, N'-(4-fluorophenyl)-hydrazide;
1-methyl-2-oxo-1,2-dihydropyridine-4-carboxylic acid, N'-(4-fluorophenyl)-hydrazide; and
1-methyl-6-oxo-1,6-dihydropyridine-3-carboxylic acid, N'-(4-fluorophenyl)-hydrazide;

or a pharmaceutically acceptable salt, or solvate thereof.

27. A process for the preparation of a compound of claim 1, comprising reacting a compound of formula (II)

with a compound of formula (III) or a pharmaceutically acceptable salt or solvate thereof

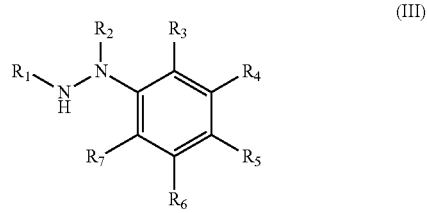

wherein A, and $R_1$ to $R_7$, $R_{12}$ and $R_{13}$ are defined above.

* * * * *